(12) United States Patent
Hon

(10) Patent No.: US 12,138,386 B2
(45) Date of Patent: Nov. 12, 2024

(54) ELECTRONIC CIGARETTE

(71) Applicant: FONTEM VENTURES B.V., Amsterdam (NL)

(72) Inventor: Lik Hon, Beijing (CN)

(73) Assignee: FONTEM VENTURES B.V., Amsterdam (NL)

( * ) Notice: Subject to any disclaimer, the term of this patent is extended or adjusted under 35 U.S.C. 154(b) by 1001 days.

(21) Appl. No.: 17/124,209

(22) Filed: Dec. 16, 2020

(65) Prior Publication Data

US 2021/0137161 A1     May 13, 2021

Related U.S. Application Data

(60) Continuation of application No. 16/839,004, filed on Apr. 2, 2020, now Pat. No. 11,013,870, which is a
(Continued)

(30) Foreign Application Priority Data

Apr. 14, 2004     (CN) .......................... 200420031182.0

(51) Int. Cl.
*A24F 40/10*     (2020.01)
*A24B 15/16*     (2020.01)
(Continued)

(52) U.S. Cl.
CPC ......... *A61M 15/0085* (2013.01); *A24B 15/16* (2013.01); *A24F 40/40* (2020.01); *A24F 40/42* (2020.01); *A24F 40/50* (2020.01); *A61M 11/005* (2013.01); *A61M 11/042* (2014.02); *A61M 11/044* (2014.02); *A61M 15/06* (2013.01);
(Continued)

(58) Field of Classification Search
CPC ............ A61M 15/0085; A61M 11/042; A61M 11/044; A61M 16/0003; A61M 11/005; A61M 15/06; A61M 2016/0024; A61M 2016/0027; A61M 2205/3653; A61M 2205/587; A61M 2205/8206; A61M 2205/8256; A24F 40/40; A24F 40/42; A24F 40/50; A24F 40/10; A24F 40/05; A24B 15/16; F24H 3/002; H05B 1/0291; H05B 3/0004; H05B 3/0014
See application file for complete search history.

(56) References Cited

U.S. PATENT DOCUMENTS 705,919 A     7/1902   Gill
1,016,844 A   2/1912   Moonelis
(Continued)

FOREIGN PATENT DOCUMENTS

AU     2004234199     11/2004
BR        9406968      8/1996
(Continued)

OTHER PUBLICATIONS

U.S. Appl. No. 16/946,289, Notice of Allowance, Jan. 12, 2021.
(Continued)

*Primary Examiner* — Dionne W. Mayes
(74) *Attorney, Agent, or Firm* — Perkins Coie LLP; Kenneth H. Ohriner

(57) ABSTRACT

An electronic cigarette includes a shell and a mouthpiece. The external wall of the shell has an air inlet. An atomizer and a liquid-supply are in contact with each other. The air inlet, atomizer, and an aerosol passage are interconnected.

10 Claims, 5 Drawing Sheets

Related U.S. Application Data continuation of application No. 16/440,956, filed on Jun. 13, 2019, now Pat. No. 10,701,982, which is a continuation of application No. 15/990,773, filed on May 28, 2018, now Pat. No. 10,349,682, which is a continuation of application No. 14/525,066, filed on Oct. 27, 2014, now Pat. No. 10,238,144, which is a continuation of application No. 13/777,927, filed on Feb. 26, 2013, now Pat. No. 8,893,726, which is a division of application No. 13/560,789, filed on Jul. 27, 2012, now Pat. No. 8,490,628, which is a continuation of application No. 12/944,123, filed on Nov. 11, 2010, now Pat. No. 8,393,331, which is a continuation of application No. 10/587,707, filed as application No. PCT/CN2005/000337 on Mar. 18, 2005, now Pat. No. 7,832,410.

(51) Int. Cl.

| | | |
|---|---|---|
| *A24F 40/40* | (2020.01) | |
| *A24F 40/42* | (2020.01) | |
| *A24F 40/50* | (2020.01) | |
| *A61M 11/00* | (2006.01) | |
| *A61M 11/04* | (2006.01) | |
| *A61M 15/00* | (2006.01) | |
| *A61M 15/06* | (2006.01) | |
| *A61M 16/00* | (2006.01) | |
| *F24H 3/00* | (2022.01) | |
| *H05B 1/02* | (2006.01) | |
| *H05B 3/00* | (2006.01) | |
| *A24F 40/05* | (2020.01) | |

(52) U.S. Cl.
CPC ......... *A61M 16/0003* (2014.02); *F24H 3/002* (2013.01); *H05B 1/0291* (2013.01); *H05B 3/0004* (2013.01); *H05B 3/0014* (2013.01); *A24F 40/05* (2020.01); *A24F 40/10* (2020.01); *A61M 2016/0024* (2013.01); *A61M 2016/0027* (2013.01); *A61M 2205/3653* (2013.01); *A61M 2205/587* (2013.01); *A61M 2205/8206* (2013.01); *A61M 2205/8256* (2013.01)

(56) References Cited

U.S. PATENT DOCUMENTS

| | | |
|---|---|---|
| 1,147,416 A | 7/1915 | MacDonald |
| 1,514,682 A | 11/1924 | Wilson |
| 1,775,947 A | 5/1927 | Robinson |
| 2,057,353 A | 10/1936 | Whittemore |
| 2,631,219 A | 3/1953 | Suchy |
| 3,200,819 A | 8/1965 | Gilbert |
| 3,385,303 A | 5/1968 | Hind |
| 3,428,053 A | 2/1969 | Schoenbaum |
| 3,431,393 A | 3/1969 | Katsuda |
| 3,471,120 A | 10/1969 | Geiselman |
| 3,479,561 A | 11/1969 | Janning |
| 3,685,522 A | 8/1972 | Kleinhans |
| 3,747,120 A | 7/1973 | Stemme |
| 3,860,012 A | 1/1975 | Selke |
| 3,952,798 A | 4/1976 | Jacobson |
| 4,030,083 A | 6/1977 | Boll |
| 4,171,000 A | 10/1979 | Uhle |
| 4,270,552 A | 6/1981 | Jenkins |
| 4,589,428 A | 5/1986 | Keritsis |
| 4,641,053 A | 2/1987 | Takeda |
| 4,676,237 A | 6/1987 | Wood |
| 4,712,295 A | 12/1987 | Peele |
| 4,735,217 A | 4/1988 | Gerth |
| 4,756,318 A | 7/1988 | Clearman |
| 4,771,295 A | 9/1988 | Baker |
| 4,771,796 A | 9/1988 | Myer |
| 4,797,692 A | 1/1989 | Ims |
| 4,848,374 A | 7/1989 | Chard |
| 4,878,506 A | 11/1989 | Pinck |
| 4,909,939 A | 3/1990 | Rickelton |
| 4,945,448 A | 7/1990 | Bremenour |
| 4,945,929 A | 8/1990 | Egilmex |
| 4,945,931 A | 8/1990 | Gori |
| 4,947,874 A | 8/1990 | Brooks |
| 4,947,875 A | 8/1990 | Brooks |
| 4,968,263 A | 11/1990 | Silbernagel |
| 4,976,692 A | 12/1990 | Atad |
| 4,981,522 A | 1/1991 | Nichols |
| 4,990,939 A | 2/1991 | Sekiya |
| 5,036,633 A | 8/1991 | Kobori |
| 5,042,470 A | 8/1991 | Kanesaka |
| 5,060,671 A | 10/1991 | Counts et al. |
| 5,095,921 A | 3/1992 | Losee |
| 5,124,200 A | 6/1992 | Mallonee |
| 5,129,409 A | 7/1992 | White |
| 5,144,962 A | 9/1992 | Counts |
| 5,159,940 A | 11/1992 | Hayward et al. |
| 5,162,263 A | 11/1992 | Counts |
| 5,179,966 A | 1/1993 | Losee |
| 5,224,264 A | 7/1993 | Dux |
| 5,249,586 A | 10/1993 | Morgan |
| 5,261,424 A | 11/1993 | Sprinkel |
| 5,266,746 A | 11/1993 | Nishihara |
| 5,322,075 A | 6/1994 | Deevi |
| 5,432,251 A | 7/1995 | Grosse-Bley et al. |
| 5,438,978 A | 8/1995 | Hardester, III |
| 5,497,791 A | 3/1996 | Bowen |
| 5,505,214 A | 4/1996 | Collins |
| 5,591,368 A | 1/1997 | Fleischhauer |
| 5,666,977 A | 9/1997 | Higgins |
| 5,666,978 A | 9/1997 | Counts |
| 5,703,633 A | 12/1997 | Gehrer |
| 5,730,158 A | 3/1998 | Collins |
| 5,743,251 A | 4/1998 | Howell |
| 5,745,985 A | 5/1998 | Ghosh |
| 5,799,663 A | 9/1998 | Gross |
| 5,819,756 A | 10/1998 | Mielordt |
| 5,894,841 A | 4/1999 | Voges |
| 5,944,025 A | 8/1999 | Cook |
| 5,996,589 A | 12/1999 | St. Charles |
| 6,010,052 A | 1/2000 | Leins et al. |
| 6,019,921 A | 2/2000 | Lutz |
| 6,040,560 A | 3/2000 | Fleischhauer |
| 6,155,268 A | 12/2000 | Takeuchi |
| 6,196,218 B1 | 3/2001 | Voges |
| 6,234,167 B1 | 5/2001 | Cox |
| 6,260,549 B1 | 7/2001 | Sosiak |
| 6,322,268 B1 | 11/2001 | Kaufmann |
| 6,354,293 B1 | 3/2002 | Madison |
| 6,357,671 B1 | 3/2002 | Cewers |
| 6,443,146 B1 | 9/2002 | Voges |
| 6,501,052 B2 | 12/2002 | Cox |
| 6,598,607 B2 | 7/2003 | Adiga |
| 6,601,776 B1 | 8/2003 | Oljaca |
| 6,619,284 B2 | 9/2003 | Kong |
| 6,620,659 B2 | 9/2003 | Emmma |
| 6,701,921 B2 | 3/2004 | Sprinkel |
| 6,810,883 B2 | 11/2004 | Felter |
| 6,854,461 B2 | 2/2005 | Nichols |
| 6,854,470 B1 | 2/2005 | Pu |
| 7,100,618 B2 | 9/2006 | Dominguez |
| 7,284,424 B2 | 10/2007 | Kanke |
| 7,315,599 B1 | 1/2008 | Morriss |
| 7,726,320 B2 | 6/2010 | Robinson |
| 7,830,031 B2 | 11/2010 | Helle et al. |
| 7,832,410 B2 | 11/2010 | Hon |
| 7,997,280 B2 | 8/2011 | Rosenthal |
| 8,156,944 B2 | 4/2012 | Han |
| 8,511,318 B2 | 8/2013 | Hon |
| 9,326,548 B2 | 5/2016 | Hon |
| 9,326,550 B2 | 5/2016 | Hon |
| 9,339,062 B2 | 5/2016 | Hon |
| 9,370,205 B2 | 6/2016 | Hon |
| 10,045,564 B2 | 8/2018 | Hon |
| 10,085,489 B2 | 10/2018 | Hon |

(56) References Cited

U.S. PATENT DOCUMENTS

| | | | |
|---|---|---|---|
| 10,178,881 | B2 | 1/2019 | Hon |
| 10,349,682 | B2 | 7/2019 | Hon |
| 10,701,982 | B2 | 7/2020 | Hon |
| 10,893,705 | B2 | 1/2021 | Hon |
| 2002/0170566 | A1 | 11/2002 | Farr |
| 2003/0011579 | A1 | 1/2003 | Gong |
| 2003/0108342 | A1 | 6/2003 | Sherwood |
| 2003/0109342 | A1 | 6/2003 | Sherwood |
| 2003/0150446 | A1 | 8/2003 | Patel |
| 2004/0099266 | A1 | 5/2004 | Cross |
| 2004/0149282 | A1 | 8/2004 | Hickle |
| 2005/0016550 | A1 | 1/2005 | Katase |
| 2006/0016453 | A1 | 1/2006 | Kim |
| 2007/0125765 | A1 | 6/2007 | Nelson |
| 2007/0267031 | A1 | 11/2007 | Hon |

FOREIGN PATENT DOCUMENTS

| | | |
|---|---|---|
| CN | 1135860 A | 11/1996 |
| CN | 2293957 Y | 10/1998 |
| CN | 1233436 | 11/1999 |
| CN | 1252961 A | 5/2000 |
| CN | 1530041 A | 9/2004 |
| CN | 1575673 A | 2/2005 |
| CN | 2719043 | 8/2005 |
| CN | 1541577 A | 9/2006 |
| CN | 201067079 Y | 6/2008 |
| CN | 201085044 Y | 7/2008 |
| CN | 201797997 Y | 4/2011 |
| CN | 202026802 Y | 11/2011 |
| CN | 202026804 Y | 11/2011 |
| EP | 0342538 A | 11/1989 |
| EP | 0358002 A2 | 3/1990 |
| EP | 0358114 A2 | 3/1990 |
| EP | 0230420 B1 | 3/1991 |
| EP | 0295122 B1 | 1/1992 |
| EP | 0488488 B1 | 3/1992 |
| EP | 0545186 A2 | 6/1993 |
| EP | 0619761 A1 | 10/1994 |
| EP | 0430566 B1 | 4/1995 |
| EP | 0703735 A1 | 4/1996 |
| EP | 0845220 A1 | 6/1998 |
| EP | 0951219 A1 | 11/2002 |
| EP | 0845220 B1 | 9/2003 |
| EP | 1736065 A1 | 12/2006 |
| JP | H9-326299 A | 12/1997 |
| JP | 2001-291598 A | 10/2001 |
| WO | WO1986002528 A2 | 5/1986 |
| WO | WO1994009842 A1 | 5/1994 |
| WO | WO1994021317 A1 | 9/1994 |
| WO | WO1997040876 A2 | 11/1997 |
| WO | WO1998017130 A1 | 4/1998 |
| WO | WO2001005459 A1 | 1/2001 |
| WO | WO2001032247 A1 | 5/2001 |
| WO | WO2003055486 A1 | 7/2003 |
| WO | WO2003101454 A1 | 12/2003 |
| WO | WO2004023222 A2 | 3/2004 |
| WO | WO2004080216 A1 | 3/2004 |
| WO | WO2004043175 A1 | 5/2004 |
| WO | WO2004095955 | 11/2004 |

OTHER PUBLICATIONS

U.S. Appl. No. 16/846,255, Non-Final Office Action, Mar. 3, 2021.
CN Creative and Intellicig USA, CV11-6268 Invalidity Contentions, Apr. 12, 2012.
Collins, John M., Expert Report—Invalidity (Excerpts), CV14-01645, Jun. 18, 2015.
Collins, John M., Expert Report—Invalidity, CV14-01645-Appendix G-'331, Jun. 18, 2015.
Collins, John M., Expert Report—Invalidity, CV14-01645-Appendix H-'628, Jun. 18, 2015.
Collins, John M., Expert Report—Invalidity, CV14-01645-Appendix K-1-'726, Jun. 18, 2015.
Collins, John M., Expert Report—Invalidity, CV14-01645-Appendix K-2-'726, Jun. 18, 2015.
Collins, John M., Expert Report—Invalidity, CV14-01645-Appendix K-3-'726, Jun. 18, 2015.
Collins, John M., Expert Report—Invalidity, CV14-01645-Appendix K-4-'726, Jun. 18, 2015.
Collins, John M., Expert Report—Invalidity, CV14-01645-Appendix K-5-'726, Jun. 18, 2015.
Collins, John M., Expert Report—Invalidity, CV14-01645-Appendix K-6-'726, Jun. 18, 2015.
Cyphert Gil DBA NU1S, CV11-0367 Invalidity Contentions, Apr. 12, 2012.
European Patent Office, Supplemental European Search Report for EP05729107, Jul. 31, 2007.
European Patent Office, Supplemental Partial European Search Reports for EP05729107, May 22, 2007.
Hewlett-Packard, Thermal Ink—Jet Print Cartridge Designers Guide (2nd Edition), Jan. 12, 1995.
Introduction to selecting and using electronic components, ISBN7-111-13752-3, exact publication date unknown, believed to be publicly available at least as early as Jun. 2006.
IP Office Australia, Examiner's Report for AU 2005232354, Jan. 12, 2010.
IP Office Australia, Search and Examination Report for SG200604498-6, Apr. 16, 2008.
IP Office Brazil, BR PI0506780-4, Office Action with Search Report, with informal English translation, Jul. 19, 2016.
State Intellectual Property Office, PRC China, Reexamination Decision on the Request for Invalidation for CN200420031182.0 by Shenzhen Smoore Technology, Jun. 22, 2009 with English translation.
State Intellectual Property Office, PRC China, Search Report for PCT/CN2005/000337, Jul. 14, 2005.
IP Office India, Application No. 3872/DELNP/2006, Hearing Notice, Sep. 4, 2019.
ITC Limited, Pre-Grant Opposition against IN3872/DELNP/2006, Aug. 11, 2014, 19 pgs.
Manual for Electric Engineers, 2nd Ed, Mar. 2000.
Manual for Mechanical Designers, 4th Ed, Jan. 2002.
Materials Manual—Nonmetal, Jul. 1, 1985.
NJOY, Inc. et al, Defendants' Joint Invalidity Contentions, CV14-01645 etc., Aug. 7, 2014 (see pp. 7-16).
NJOY, Inc. et al., Defendants' Joint Invalidity Contentions, CV-14-01645 etc., Attachment B—Claim Charts for Patent 8393331, Aug. 7, 2014.
NJOY, Inc. et al., Defendants' Joint Invalidity Contentions, CV-14-01645 etc., Attachment C—Claim Charts for Patent 8490628, Aug. 7, 2014.
NJOY, Inc. et al, Defendants' Joint Invalidity Contentions, CV14-01645 etc., Feb. 26, 2015.
NJOY, Inc. et al, Defendant's Joint Invalidity Contentions, CV14-01645 etc., Exhibit B—Claim Charts for Patent 8893726—Feb. 26, 2015.
NJOY, Inc.'s Declaration of Brent K. Yamashita in Support of Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.
NJOY, Inc.'s Exhibit 1 to Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.
NJOY, Inc.'s Exhibit 2 to Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.
NJOY, Inc.'s Exhibit 3 to Defendants' Motion for Leave to Amend Invalidity Contentions dated Jun. 29, 2015 and filed in *Fontem Ventures B.V. v. NJOY, Inc.*, U.S. District Court, Central District of California, Consolidated Case No. CV 14-01645 GW (MRW) and related consolidated cases.

(56) References Cited

OTHER PUBLICATIONS

NJOY, Inc.'s Exhibit 4 to Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc.'s Exhibit 5 to Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc.'s Memorandum of Points and Authorities in Support of Defendants' Motion for Leave to Amend Invalidity Contentions dated Jun. 29, 2015 and filed in *Fontem Ventures B.V.* v. *NJOY, Inc.*, U.S. District Court, Central District of California, Consolidated Case No. CV 14-01645 GW (MRW) and related consolidated cases.
NJOY. Inc.'s production documents VLACHOS 0000061-72; *Fontem Ventures B.V.* v. *NJOY, Inc.*, U.S. District Court, Central District of California, Consolidated Case No. CV 14-01645 GW (MRW) and related consolidated cases, Mar. 16, 2001.
NJOY. Inc.'s Reply Brief in Support of Defendants' Motion for Leave to Amend Invalidity Contentions dated Jul. 13, 2015 and filed in *Fontem Ventures B.V.* v. *NJOY, Inc.*, U.S. District Court, Central District of California, Consolidated Case No. CV 14-01645 GW (MRW) and related consolidated cases.
NJOY, Inc., IPR2014-01289, Paper 1, Petition for Inter Partes Review of U.S. Pat. No. 8,393,331, Aug. 14, 2014.
NJOY, Inc., IPR2014-01289, Exhibit 1001 U.S. Pat. No. 8,393,331 ("the '331 patent"), Aug. 14, 2014.
NJOY, Inc., IPR2014-01289, Exhibit 1002 U.S. Pat. No. 8,393,331 File History ("File History"), Aug. 14, 2014.
NJOY, Inc., IPR2014-01289, Exhibit 1003 U.S. Pat. No. 6,155,268 ("Takeuchi"), Aug. 14, 2014.
NJOY, Inc., IPR2014-01289, Exhibit 1004 U.S. Patent No. 6,234,167("Cox"), Aug. 14, 2014.
NJOY, Inc., IPR2014-01289, Exhibit 1005 U.S. Pat. No. 5,894,841 ("Voges"), Aug. 14, 2014.
NJOY, Inc., IPR2014-01289, Exhibit 1006 U.S. Pat. No. 4,990,939 ("Sekiya"), Aug. 14, 2014.
NJOY, Inc., IPR2014-01289, Exhibit 1007 U.S. Pat. No. 4,771,295 ("Baker"), Aug. 14, 2014.
NJOY, Inc., IPR2014-01289, Exhibit 1008 U.S. Pat. No. 5,743,251 ("Howell"), Aug. 14, 2014.
NJOY, Inc., IPR2014-01289, Exhibit 1009 U.S. Pat. No. 6,501,052 ("Cox '02"), Aug. 14, 2014.
NJOY, Inc., IPR2014-01289, Exhibit 1010 Thermal Ink-Jet Print Cartridge Designers Guide (2nd Edition Hewlett Packard) ("Jet Print Cartridge Designers Guide"), Aug. 14, 2014.
NJOY, Inc., IPR2014-01289, Exhibit 1011 Collins Expert Declaration, Aug. 14, 2014.
NJOY, Inc., IPR2014-01289, Exhibit 1012 U.S. Pat. No. 3,747, 120 ("Stemme"), Aug. 14, 2014.
NJOY, Inc., IPR2014-01289, Exhibit 1013 U.S. Pat. No. 4,797,692 ("Ims"), Aug. 14, 2014.
NJOY, Inc., IPR2014-01289, Exhibit 1014 U.S. Pat. No. 5,666,977 ("Higgins"), Aug. 14, 2014.
NJOY, Inc., IPR2014-01289, Exhibit 1015 U.S. Pat. No. 6,701,921 ("Sprinkel"), Aug. 14, 2014.
NJOY, Inc., IPR2014-01289, Exhibit 1016 U.S. Pat. No. 4,848,374 ("Chard"), Aug. 14, 2014.
NJOY, Inc., IPR2014-01289, Exhibit 1017 U.S. Pat. No. 5,060,671 ("Counts"), Aug. 14, 2014.
NJOY, Inc., IPR2014-01289, Exhibit 1018 European Patent No. 0,358, 114 ("Brooks"), Aug. 14, 2014.
NJOY, Inc., IPR2014-01289, Exhibit 1019 International Publication No. WO 98/17131 ("Fleischhauer"), Aug. 14, 2014.
NJOY, Inc., IPR2014-01289, Exhibit 1020 U.S. Pat. No. 6,196,218 ("Voges II"), Aug. 14, 2014.
NJOY, Inc., IPR2014-01289, Exhibit 1021 U.S. Pat. No. 3,431,393 ("Katsuda"), Aug. 14, 2014.
NJOY, Inc., IPR2014-01289, Exhibit 1022 Certified English Translation of Chinese Publication No. CN1233436 ("Hongbin").
NJOY, Inc., IPR2014-01289, Exhibit 1023 U.S. Pat. No. 6,598,607 ("Adiga"), Aug. 14, 2014.
NJOY, Inc., IPR2014-01289, Exhibit 1024 U.S. Pat. No. 4,945,448 ("Bremenour"), Aug. 14, 2014.
NJOY, Inc., IPR2014-01289, Exhibit 1025 U.S. Pat. No. 2,057,353 ("Whittemore"), Aug. 14, 2014.
NJOY, Inc., IPR2014-01289, Exhibit 1026 ANDRUS, Canadian Respiratory Journal Nov.-Dec. 1999;6(6), p. 509 ("Nicotine Microaerosol Inhaler"), Aug. 14, 2014.
NJOY, Inc., IPR2014-01289, Exhibit 1027 U.S. Pat. No. 6,471,782 ("Fang"), Aug. 14, 2014.
NJOY, Inc., IPR2014-01289, Exhibit 1028 International Publication No. WO 2003000324 A1 ("Karl"), Aug. 14, 2014.
NJOY, Inc., IPR2014-01289, Exhibit 1029 U.S. Pat. No. 6,062,213 ("Fuisz"), Aug. 14, 2014.
NJOY, Inc., IPR2014-01289, Exhibit 1030 International Publication No. WO 2002098390 A2 ("Hodges"), Aug. 14, 2014.
NJOY, Inc., IPR2014-01289, Exhibit 1031 U.S. Pat. No. 5,745,985 ("Ghosh"), Aug. 14, 2014.
NJOY, Inc., IPR2014-01289, Exhibit 1032 U.S. Pat. No. 4,676,237 ("Wood"), Aug. 14, 2014.
NJOY, Inc., IPR2014-01289, Exhibit 1033 U.S. Pat. No. 5,327,915 ("Porenski"), Aug. 14, 2014.
NJOY, Inc., IPR2014-01289, Exhibit 1034 U.S. Pat. No. 7,284,424 ("Kanke"), Aug. 14, 2014.
NJOY, Inc., IPR2014-01289, Exhibit 1035 U.S. Pat. No. 5,224,265 ("Dux"), Aug. 14, 2014.
NJOY, Inc., IPR2014-01289, Exhibit 1036 U.S. Pat. No. 6,620,659 ("Emmma"), Aug. 14, 2014.
NJOY, Inc., IPR2014-01289, Exhibit 1037 U.S. Pat. No. 3,400,998 ("Daugherty"), Aug. 14, 2014.
NJOY, Inc., IPR2014-01289, Exhibit 1038 European Patent Application No. EP0845220 B1 ("Susa"), Aug. 14, 2014.
NJOY, Inc., IPR2014-01289, Exhibit 1039 U.S. Pat. No. 5,703,633 ("Gehrer"), Aug. 14, 2014.
NJOY, Inc., IPR2014-01289, Exhibit 1040 U.S. Pat. No. 3,200,819 ("Gilbert"), Aug. 14, 2014.
NJOY, Inc., IPR2014-01289, Exhibit 1041 U.S. Pat. No. 3,502,588 ("Winberg"), Aug. 14, 2014.
NJOY, Inc., IPR2014-01289, Exhibit 1042 U.S. Pat. No. 3,203,025 ("Schreur"), Aug. 14, 2014.
NJOY, Inc., IPR2014-01289, Exhibit 1043 U.S. Pat. No. 4,945,929 ("Egilmex"), Aug. 14, 2014.
NJOY, Inc., IPR2014-01289, Exhibit 1044 U.S. Pat. No. 5,124,200 ("Mallonee"), Aug. 14, 2014.
NJOY, Inc., IPR2014-01289, Exhibit 1045 U.S. Patent App. Pub. No. 20060093977 A1 ("Pellizzari"), Aug. 14, 2014.
NJOY, Inc., IPR2014-01289, Exhibit 1046 U.S. Pat. No. 7,059,307 ("Pellizzari II"), Aug. 14, 2014.
NJOY, Inc., IPR2014-01289, Exhibit 1047 U.S. Pat. No. 5,996,589 ("St. Charles"), Aug. 14, 2014.
NJOY, Inc., IPR2014-01289, Exhibit 1048 U.S. Pat. No. 4,972,855 ("Kuriyama"), Aug. 14, 2014.
NJOY, Inc., IPR2014-01289, Exhibit 1049 Declaration of Dr. Saurabh Gupta, Aug. 14, 2014.
NJOY, Inc., IPR2014-01300, Paper 2, Petition for Inter Partes Review of U.S. Pat. No. 8,490,628, Aug. 15, 2014.
NJOY, Inc., IPR2014-01300, Exhibit 1001 U.S. Pat. No. 8,490,628 ("the '628 patent"), Aug. 15, 2014.
NJOY, Inc., IPR2014-01300, Exhibit 1002 U.S. Pat. No. 8,490,628 File History ("File History"), Aug. 15, 2014.
NJOY, Inc., IPR2014-01300, Exhibit 1003 U.S. Pat. No. 6,155,268 ("Takeuchi"), Aug. 15, 2014.
NJOY, Inc., IPR2014-01300, Exhibit 1004 U.S. Pat. No. 2,057,353 ("Whittemore"), Aug. 15, 2014.
NJOY, Inc., IPR2014-01300, Exhibit 1005 U.S. Pat. No. 7,143,766 ("Schuster"), Aug. 15, 2014.
NJOY, Inc., IPR2014-01300, Exhibit 1006 U.S. Pat. No. 5,996,589 ("St. Charles"), Aug. 15, 2014.
NJOY, Inc., IPR2014-01300, Exhibit 1007 U.S. Pat. No. 6,598,607 ("Adiga"), Aug. 15, 2014.

(56) References Cited

OTHER PUBLICATIONS

NJOY, Inc., IPR2014-01300, Exhibit 1008 European Patent Application No. EP0845220 B1 ("Susa"), Aug. 15, 2014.
NJOY, Inc., IPR2014-01300, Exhibit 1009 U.S. Pat. No. 3,200,819 ("Gilbert"), Aug. 15, 2014.
NJOY, Inc., IPR2014-01300, Exhibit 1010 U.S. Pat. No. 3,060,429 ("Winston"), Aug. 15, 2014.
NJOY, Inc., IPR2014-01300, Exhibit 1011 U.S. Pat. No. 5,894,841 ("Voges"), Aug. 15, 2014.
NJOY, Inc., IPR2014-01300, Exhibit 1012 U.S. Pat. No. 5,703,633 ("Gehrer"), Aug. 15, 2014.
NJOY, Inc., IPR2014-01300, Exhibit 1013 Thermal Ink-Jet Print Cartridge Designers Guide (2nd Edition Hewlett Packard) ("Jet Print Cartridge Designers Guide"), Aug. 15, 2014.
NJOY, Inc., IPR2014-01300, Exhibit 1014 U.S. Pat. No. 5,666,977 ("Higgins"), Aug. 15, 2014.
NJOY, Inc., IPR2014-01300, Exhibit 1015 U.S. Pat. No. 6,701,921 ("Sprinkel"), Aug. 15, 2014.
NJOY, Inc., IPR2014-01300, Exhibit 1016 U.S. Pat. No. 4,848,374 ("Chard"), Aug. 15, 2014.
NJOY, Inc., IPR2014-01300, Exhibit 1017 U.S. Pat. No. 5,060,671 ("Counts"), Aug. 15, 2014.
NJOY, Inc., IPR2014-01300, Exhibit 1018 European Patent No. 0,358, 114 ("Brooks"), Aug. 15, 2014.
NJOY, Inc., IPR2014-01300, Exhibit 1019 International Publication No. WO 98/17131 ("Fleischhauer"), Aug. 15, 2014.
NJOY, Inc., IPR2014-01300, Exhibit 1020 U.S. Patent No. 6,196,218 ("Voges II"), Aug. 15, 2014.
NJOY, Inc., IPR2014-01300, Exhibit 1021 U.S. Pat. No. 3,431,393 ("Katsuda"), Aug. 15, 2014.
NJOY, Inc., IPR2014-01300, Exhibit 1022 Certified English Translation of Chinese Publication No. CN1233436 ("Hongbin"), Aug. 15, 2014.
NJOY, Inc., IPR2014-01300, Exhibit 1023 ANDRUS, Canadian Respiratory Journal Nov.-Dec. 1999;6(6), p. 509 ("Nicotine Microaerosol Inhaler"), Aug. 15, 2014.
NJOY, Inc., IPR2014-01300, Exhibit 1024 U.S. Pat. No. 4,972,855 ("Kuriyama"), Aug. 15, 2014.
NJOY, Inc., IPR2014-01300, Exhibit 1025 U.S. Pat. No. 6,322,268 ("Kaufman"), Aug. 15, 2014.
NJOY, Inc., IPR2014-01300, Exhibit 1026 U.S. Pat. No. 6,722,763 ("Hsu"), Aug. 15, 2014.
NJOY, Inc., IPR2014-01300, Exhibit 1027 U.S. Pat. No. 5,646,666 ("Cowger"), Aug. 15, 2014.
Njoy, Inc., IPR2014-01300, Exhibit 1028 U.S. Pat. No. 8,393,331 File History ("331 FileHistory"), Aug. 15, 2014.
NJOY, Inc., IPR2014-01300, Exhibit 1029 U.S. Pat. No. 4,945,448 ("Bremenour").
NJOY, Inc., IPR2014-01300, Exhibit 1030 U.S. Pat. No. 3,400,998 ("Daugherty"), Aug. 15, 2014.
NJOY, Inc., IPR2014-01300, Exhibit 1031 U.S. Pat. No. 5,745,985 ("Ghosh"), Aug. 15, 2014.
NJOY, Inc., IPR2014-01300, Exhibit 1032 U.S. Pat. No. 4,676,237 ("Wood"), Aug. 15, 2014.
NJOY, Inc., IPR2014-01300, Exhibit 1033 U.S. Pat. No. 5,327,915 ("Porenski"), Aug. 15, 2014.
NJOY, Inc., IPR2014-01300, Exhibit 1034 U.S. Pat. No. 7,284,424 ("Kanke"), Aug. 15, 2014.
NJOY, Inc., IPR2014-01300, Exhibit 1035 U.S. Pat. No. 5,224,265 ("Dux"), Aug. 15, 2014.
NJOY, Inc., IPR2014-01300, Exhibit 1036 U.S. Pat. No. 6,620,659 ("Emmma"), Aug. 15, 2014.
NJOY, Inc., IPR2014-01300, Exhibit 1037 U.S. Pat. No. 6,234,167("Cox"), Aug. 15, 2014.
NJOY, Inc., IPR2014-01300, Exhibit 1038 U.S. Pat. No. 4,990,939 ("Sekiya"), Aug. 15, 2014.
NJOY, Inc., IPR2014-01300, Exhibit 1039 U.S. Pat. No. 4,771,295 ("Baker"), Aug. 15, 2014.
NJOY, Inc., IPR2014-01300, Exhibit 1040—Collins Expert Declaration, Aug. 15, 2014.
NJOY, Inc., IPR2014-01300, Exhibit 1041 U.S. Pat. No. 5,743,251 ("Howell"), Aug. 15, 2014.
NJOY, Inc., IPR2014-01300, Exhibit 1042 U.S. Pat. No. 6,501,052 ("Cox '02"), Aug. 15, 2014.
NJOY, Inc., IPR2014-01300, Exhibit 1043 U.S. Pat. No. 4,797,692 ("Ims"), Aug. 15, 2014.
NJOY, Inc., IPR2014-01300, Exhibit 1044 U.S. Pat. No. 6,471,782 ("Fang"), Aug. 15, 2014.
NJOY, Inc., IPR2014-01300, Exhibit 1045 International Publication No. WO 2003000324 A1 ("Karl"), Aug. 15, 2014.
NJOY, Inc., IPR2014-01300, Exhibit 1046 International Publication No. WO 2002098390 A2 ("Hodges"), Aug. 15, 2014.
NJOY, Inc., IPR2014-01300, Exhibit 1047 U.S. Pat. No. 6,062,213 ("Fuisz"), Aug. 15, 2014.
NJOY, Inc., IPR2014-01300, Exhibit 1048 U.S. Application Publication Patent No. 2006/0093977 A1 ("Pellizzari"), Aug. 15, 2014.
NJOY, Inc., IPR2014-01300, Exhibit 1049 U.S. Pat. No. 7,059,307 B2 ("Pellizzari II"), Aug. 15, 2014.
NJOY, Inc., IPR2014-01300, Exhibit 1050 U.S. Pat. No. 3,203,025 ("Schreur"), Aug. 15, 2014.
NJOY, Inc., IPR2014-01300, Exhibit 1051 U.S. Application Publication Patent No. 2001/0026788 ("Piskorz"), Aug. 15, 2014.
NJOY, Inc., IPR2014-01300, Exhibit 1052 U.S. Pat. No. 6,102,036 ("Slutsky"), Aug. 15, 2014.
NJOY, Inc., IPR2014-01300, Exhibit 1053 U.S. Pat. No. 3,502,588 ("Winberg"), Aug. 15, 2014.
NJOY, Inc., IPR2014-01300, Exhibit 1054 U.S. Pat. No. 4,945,929 ("Egilmex"), Aug. 15, 2014.
NJOY, Inc., IPR2014-01300, Exhibit 1055 U.S. Pat. No. 5,124,200 ("Mallonee"), Aug. 15, 2014.
NJOY, Inc., IPR2014-01300, Exhibit 1056 Declaration of Dr. Saurabh Gupta, Aug. 15, 2014.
NJOY, Inc. et al, IPR2015-01302, Paper 2, Petition for Inter Partes Review of U.S. Pat. No. 8,893,726, May 29, 2015.
NJOY, Inc. et al., IPR2015-01302, Exhibit 1001 U.S. Pat. No. 8,893,726 ("the '726 patent"), May 29, 2015.
NJOY, Inc. et al., IPR2015-01302, Exhibit 1002—Nayfeh Expert Declaration, May 29, 2015.
NJOY, Inc. et al., IPR2015-01302, Exhibit 1003 U.S. Pat. No. 6,155,268 ("Takeuchi"), May 29, 2015.
NJOY, Inc. et al., IPR2015-01302, Exhibit 1004 U.S. Pat. No. 5, 144,962 ("Counts"), May 29, 2015.
NJOY, Inc. et al., IPR2015-01302, Exhibit 1005 U.S. Pat. No. 6,322,268 ("Kaufmann"), May 29, 2015.
NJOY, Inc. et al., IPR2015-01302, Exhibit 1006 '726 Patent File History, Non-Final Rejection (Aug. 16, 2013), May 29, 2015.
NJOY, Inc. et al., IPR2015-01302, Exhibit 1007 '726 Patent File History, Notice of Allowance (Aug. 18, 2014), May 29, 2015.
NJOY, Inc. et al., IPR2015-01302, Exhibit 1008 '726 Patent File History, Collected Info. Disclosure Statements, May 29, 2015.
NJOY, Inc. et al., IPR2015-01302, Exhibit 1009 Markman Hearing/ Claim Construction Order, *Fontem Ventures, B.V.* v. *NJOY, Inc.*, No. 14-cv-1645, Dkt. 133 (C.D. Cal. May 7, 2015), May 29, 2015.
NJOY, Inc. et al., IPR2015-01302, Exhibit 1010 Rulings on Claim Construction, *Fontem Ventures, B.V.* v. *NJOY, Inc.*, No. 14-cv-1645, Dkt. 65 (C.D. Cal. Jan. 29, 2015), May 29, 2015.
NJOY, Inc. et al., IPR2015-01302, Exhibit 1011 Joint Claim Construction and Prehearing Statement, *Fontem Ventures, B.V.* v. *NJOY, Inc.*, No. 14-cv-1645, Dkt. 93 (C.D. Cal. Mar. 19, 2015), May 29, 2015.
NJOY, Inc. et al., IPR2015-01302, Exhibit 1012 Revised Joint Claim Construction and Prehearing Statement, *Fontem Ventures, B.V.* v. *NJOY, Inc.*, No. 14-cv-1645, Dkt. 34 (C.D. Cal. Sep. 30, 2014), May 29, 2015.
NJOY, Inc. et al., IPR2015-01302, Exhibit 1013 U.S. Pat. No. 4,945,931 ("the '931 patent"), May 29, 2015.
NJOY, Inc. et al., IPR2015-01302, Exhibit 1014 Curriculum Vitae of Samir Nayfeh, Ph.D., May 29, 2015.
Nu Mark LLC, Answer and Counterclaims in *Fontem Ventures B.V.* v. *Nu Mark LLC*, 16-CV-1259, Dkt. 034, Oct. 26, 2016.
Nu Mark LLC, Answer to Complaint and Counterclaims in *Fontem Ventures B.V.* v. *Nu Mark LLC*, 16-CV-2291, Dkt. 025, Jun. 27, 2016.

(56) References Cited

OTHER PUBLICATIONS

Nu Mark LLC, First Amended Answer and Counterclaims in *Fontem Ventures B.V. v. Nu Mark LLC*, 16-CV-2291, Dkt. 042, Jul. 28, 2016.
Nu Mark LLC, IPR2016-01283, Paper 1, Petition for Inter Partes Review of U.S. Pat. No. 8,490,628, Jun. 28, 2016.
Nu Mark LLC, IPR2016-01283, Ex. 1101 U.S. Pat. No. 8,490,628 (the "628 Patent"), Jun. 28, 2016.
Nu Mark LLC, IPR2016-01283, Ex. 1102 File History for U.S. Pat. No. 8,490,628, Jun. 28, 2016.
Nu Mark LLC, IPR2016-01283, Ex. 1103 Declaration of John M. Collins, Ph.D., Jun. 28, 2016.
Nu Mark LLC, IPR2016-01283, Ex. 1104 Curriculum Vitae of Dr. John M. Collins, Jun. 28, 2016.
Nu Mark LLC, IPR2016-01283, Ex. 1105 U.S. Pat. App. Pub. No. 2007/0267031 A1 ("Hon 031"), Jun. 28, 2016.
Nu Mark LLC, IPR2016-01283, Ex. 1106 File History for U.S. Appl. No. 12/944,123 (issued as U.S. Pat. No. 8,393,331), Jun. 28, 2016.
Nu Mark LLC, IPR2016-01283, Ex. 1107 Substitute Specification filed in U.S. Appl. No. 12/944,123 (issued as U.S. Pat. No. 8,393,331), Jun. 28, 2016.
Nu Mark LLC, IPR2016-01283, Ex. 1108 File History for U.S. Appl. No. 10/587,707 (issued as U.S. Pat. No. 7,832,410), Jun. 28, 2016.
Nu Mark LLC, IPR2016-01283, Ex. 1109 Certified Translation of CN 20040031182, Jun. 28, 2016.
Nu Mark LLC, IPR2016-01283, Ex. 1110 Decision Instituting Inter Partes Review—IPR2014-01300, Jun. 28, 2016.
Nu Mark LLC, IPR2016-01283, Ex. 1111 Claim Construction Order, Jan. 29, 2015, Jun. 28, 2016.
Nu Mark LLC, IPR2016-01283, Ex.1112 U.S. Pat. No. 7,832,410 (the "410 Patent"), Jun. 28, 2016.
Nu Mark LLC, IPR2016-01283, Ex.1113 U.S. Pat. No. 8,689,805 (the "805 Patent"), Jun. 28, 2016.
Nu Mark LLC, IPR2016-01283, Ex.1114 File History for U.S. Appl. No. 13/426,817 (issued as U.S. Pat. No. 8,689,805), Jun. 28, 2016.
Nu Mark LLC, IPR2016-01283, Ex.1115 EP 1736065 A1, Jun. 28, 2016.
Nu Mark LLC, IPR2016-01283, Ex.1116 Complaint, *Fontem Ventures B.V., et al. v. Nu Mark LLC*, Case No. 2:16-cv-02291, Jun. 28, 2016.
Nu Mark LLC, IPR2016-01283, Ex. 1117 Certified Translation of WO 2005/099494, Jun. 28, 2016.
Nu Mark LLC, IPR2016-01283, Ex.1118 WO 2005/099494 Chinese version with English abstract (face), Jun. 28, 2016.
Nu Mark LLC, IPR2016-01285, Paper 2, Petition for Inter Partes Review of U.S. Pat. No. 8,490,628, Jun. 28, 2016.
Nu Mark LLC, IPR2016-01285, Ex.1001 U.S. Pat. No. 8,490,628 ("the 628 Patent"), Jun. 28, 2016.
Nu Mark LLC, IPR2016-01285, Ex.1002 File History for U.S. Pat. No. 8,490,628, Jun. 28, 2016.
Nu Mark LLC, IPR2016-01285, Ex. 1003 Declaration of John M. Collins, Ph.D. ("Collins Decl."), Jun. 28, 2016.
Nu Mark LLC, IPR2016-01285, Ex. 1004 U.S. Pat. No. 6,155,268 ("Takeuchi"), Jun. 28, 2016.
Nu Mark LLC, IPR2016-01285, Ex. 1005 U.S. Pat. No. 2,057,353 ("Whittemore"), Jun. 28, 2016.
Nu Mark LLC, IPR2016-01285, Ex. 1006 Decision—Institution of Inter Partes Review, Case No. IPR2014-01300 ("628 Decision"), Jun. 28, 2016.
Nu Mark LLC, IPR2016-01285, Ex. 1007 File History for U.S. Pat. No. 8,393,331, Jun. 28, 2016.
Nu Mark LLC, IPR2016-01285, Ex.1008 Order to Terminate Proceedings, Case No. IPR2014-01300, Jun. 28, 2016.
Nu Mark LLC, IPR2016-01285, Ex. 1009 U.S. Pat. No. 5,743,251 ("Howell"), Jun. 28, 2016.
Nu Mark LLC, IPR2016-01285, Ex.1010 U.S. Pat. No. 6,598,607 ("Adiga"), Jun. 28, 2016.
Nu Mark LLC, IPR2016-01285, Ex. 1011 U.S. Pat. No. 5,894,841 ("Voges"), Jun. 28, 2016.
Nu Mark LLC, IPR2016-01285, Ex.1012 U.S. Pat. No. 6,322,268 ("Kaufman"), Jun. 28, 2016.
Nu Mark LLC, IPR2016-01285, Ex.1013 U.S. Pat. No. 4,771,295 ("Baker"), Jun. 28, 2016.
Nu Mark LLC, IPR2016-01285, Ex.1014 U.S. Pat. No. 5,703,633 ("Gehrer"), Jun. 28, 2016.
Nu Mark LLC, IPR2016-01285, Ex. 1015 U.S. Pat. No. 5,124,200 ("Mallonee"), Jun. 28, 2016.
Nu Mark LLC, IPR2016-01285, Ex. 1016 U.S. Pat. No. 4,797,692 ("Ims"), Jun. 28, 2016.
Nu Mark LLC, IPR2016-01285, Ex. 1017 Thermal Ink-Jet Print Cartridge Designers Guide ("Ink-Jet Guide"), Jun. 28, 2016.
Nu Mark LLC, IPR2016-01285, Ex.1018 U.S. Patent Pub. No. 2006/0093977 ("Pellizzari I"), Jun. 28, 2016.
Nu Mark LLC, IPR2016-01285, Ex. 1019 U.S. Pat. No. 7,059,307 ("Pellizzari II"), Jun. 28, 2016.
Nu Mark LLC, IPR2016-01285, Ex. 1020 U.S. Pat. No. 6,501,052 ("Cox II"), Jun. 28, 2016.
Nu Mark LLC, IPR2016-01285, Ex. 1021 U.S. Pat. No. 6,234,167 ("Cox"), Jun. 28, 2016.
Nu Mark LLC, IPR2016-01285, Ex. 1022 U.S. Pat. No. 5,666,977 ("Higgins"), Jun. 28, 2016.
Nu Mark LLC, IPR2016-01285, Ex.1023 European Patent Application No. 0358114 A2 ("Brooks 114"), Jun. 28, 2016.
Nu Mark LLC, IPR2016-01285, Ex.1024 U.S. Pat. No. 7,284,424 ("Kanke"), Jun. 28, 2016.
Nu Mark LLC, IPR2016-01285, Ex. 1025 U.S. Pat. No. 5,224,265 ("Dux"), Jun. 28, 2016.
Nu Mark LLC, IPR2016-01285, Ex. 1026 U.S. Pat. No. 6,620,659 ("Emmma"), Jun. 28, 2016.
Nu Mark LLC, IPR2016-01285, Ex. 1027 U.S. Pat. No. 5,745,985 ("Ghosh"), Jun. 28, 2016.
Nu Mark LLC, IPR2016-01285, Ex.1028 U.S. Pat. No. 4,676,237 ("Wood"), Jun. 28, 2016.
Nu Mark LLC, IPR2016-01285, Ex. 1029 U.S. Pat. No. 4,945,448 ("Bremenour"), Jun. 28, 2016.
Nu Mark LLC, IPR2016-01285, Ex. 1030 Certified Translation of Chinese Utility Model Publication No. Cn 1233436A ("Hongbin"), Jun. 28, 2016.
Nu Mark LLC, IPR2016-01285, Ex. 1031 U.S. Pat. No. 6,196,218 ("Voges II"), Jun. 28, 2016.
Nu Mark LLC, IPR2016-01285, Ex. 1032 U.S. Pat. No. 6,722,763 ("Hsu"), Jun. 28, 2016.
Nu Mark LLC, IPR2016-01285, Ex. 1033 U.S. Pat. No. 4,947,875 ("Brooks 875"), Jun. 28, 2016.
Nu Mark LLC, IPR2016-01285, Ex. 1034 U.S. Pat. No. 5,646,666 ("Cowger"), Jun. 28, 2016.
Nu Mark LLC, IPR2016-01285, Ex. 1035 U.S. Pat. No. 1,514,682 ("Wilson"), Jun. 28, 2016.
Nu Mark LLC, IPR2016-01285, Ex. 1036 U.S. Pat. No. 3,200,819 ("Gilbert"), Jun. 28, 2016.
Nu Mark LLC, IPR2016-01285, Ex. 1037 U.S. Pat. No. 6,491,233 ("Nichols"), Jun. 28, 2016.
Nu Mark LLC, IPR2016-01288, Paper 1, Petition for Inter Partes Review of U.S. Pat. No. 8,893,726, Jun. 28, 2016.
Nu Mark LLC, IPR2016-01288, Ex.1101 U.S. Pat. No. 8,893,726 (the "726 Patent"), Jun. 28, 2016.
Nu Mark LLC, IPR2016-01288, Ex.1102 File History for U.S. Pat. No. 8,893,726, Jun. 28, 2016.
Nu Mark LLC, IPR2016-01288, Ex.1103 Declaration of John M. Collins, Ph.D., Jun. 28, 2016.
Nu Mark LLC, IPR2016-01288, Ex. 1104 Curriculum Vitae of Dr. John M. Collins, Jun. 28, 2016.
Nu Mark LLC, IPR2016-01288, Ex.1105 U.S. Pat. App. Pub. No. 2007/0267031 A1 ("Hon 031"), Jun. 28, 2016.
Nu Mark LLC, IPR2016-01288, Ex.1106 File History for U.S. Appl. No. 12/944,123 (issued as U.S. Pat. No. 8,393,331), Jun. 28, 2016.
Nu Mark LLC, IPR2016-01288, Ex.1107 Substitute Specification filed in U.S. Appl. No. 12/944,123 (issued as U.S. Pat. No. 8,393,331), Jun. 28, 2016.

(56) References Cited

OTHER PUBLICATIONS

Nu Mark LLC, IPR2016-01288, Ex.1108 File History for U.S. Appl. No. 10/587,707 (issued as U.S. Pat. No. 7,832,410), Jun. 28, 2016.
Nu Mark LLC, IPR2016-01288, Ex. 1109 Certified Translation of CN 20040031182, Jun. 28, 2016.
Nu Mark LLC, IPR2016-01288, Ex.1110 Decision Denying Inter Partes Review—IPR2014-01302, Jun. 28, 2016.
Nu Mark LLC, IPR2016-01288, Ex.1112 U.S. Pat. No. 7,832,410 (the "410 Patent"), Jun. 28, 2016.
Nu Mark LLC, IPR2016-01288, Ex.1113 U.S. Pat. No. 8,689,805 (the "805 Patent"), Jun. 28, 2016.
Nu Mark LLC, IPR2016-01288, Ex.1114 File History for U.S. Appl. No. 13/426,817 (issued as U.S. Pat. No. 8,689,805), Jun. 28, 2016.
Nu Mark LLC, IPR2016-01288, Ex.1115 EP 1736065 A1, Jun. 28, 2016.
Nu Mark LLC, IPR2016-01288, Ex.1116 Complaint, *Fontem Ventures B.V., et al.* v. *Nu Mark LLC*, Case No. 2:16-cv-02291 (excerpts), Jun. 28, 2016.
Nu Mark LLC, IPR2016-01288, Ex.1117 Certified Translation of WO 2005/099494, Jun. 28, 2016.
Nu Mark LLC, IPR2016-01288, Ex.1118 WO 2005/099494 Chinese version with English abstract (face), Jun. 28, 2016.
Nu Mark LLC, IPR2016-01297, Paper 1, Petition for Inter Partes Review of U.S. Pat. No. 8,893,726, Jun. 28, 2016.
Nu Mark LLC, IPR2016-01297, Ex. 1001 U.S. Pat. No. 8,893,726 ("the 726 Patent"), Jun. 28, 2016.
Nu Mark LLC, IPR2016-01297, Ex. 1002 File History for U.S. Pat. No. 8,893,726, Jun. 28, 2016.
Nu Mark LLC, IPR2016-01297, Ex. 1003 Declaration of John M. Collins, Ph.D., Jun. 28, 2016.
Nu Mark LLC, IPR2016-01297, Ex. 1004 U.S. Pat. No. 6,155,268 ("Takeuchi"), Jun. 28, 2016.
Nu Mark LLC, IPR2016-01297, Ex. 1005 U.S. Pat. No. 2,057,353 ("Whittemore"), Jun. 28, 2016.
Nu Mark LLC, IPR2016-01297, Ex. 1006 Decision—Institution of Inter Partes Review, Case No. IPR2014-01300 ("628 Decision"), Jun. 28, 2016.
Nu Mark LLC, IPR2016-01297, Ex. 1007 Decision—Institution of Inter Partes Review, Case No. IPR2014-01289 ("331 Decision"), Jun. 28, 2016.
Nu Mark LLC, IPR2016-01297, Ex. 1008 U.S. Pat. No. 1,514,682 ("Wilson"), Jun. 28, 2016.
Nu Mark LLC, IPR2016-01297, Ex. 1009 U.S. Pat. No. 5,743,251 ("Howell"), Jun. 28, 2016.
Nu Mark LLC, IPR2016-01297, Ex. 1010 U.S. Pat. No. 6,598,607 ("Adiga"), Jun. 28, 2016.
Nu Mark LLC, IPR2016-01297, Ex. 1011 U.S. Pat. No. 5,894,841 ("Voges"), Jun. 28, 2016.
Nu Mark LLC, IPR2016-01297, Ex. 1012 U.S. Pat. No. 4,990,939 ("Sekiya"), Jun. 28, 2016.
Nu Mark LLC, IPR2016-01297, Ex. 1013 U.S. Pat. No. 4,771,295 ("Baker"), Jun. 28, 2016.
Nu Mark LLC, IPR2016-01297, Ex. 1014 U.S. Pat. No. 5,703,633 ("Gehrer"), Jun. 28, 2016.
Nu Mark LLC, IPR2016-01297, Ex. 1015 U.S. Pat. No. 5,124,200 ("Mallonee"), Jun. 28, 2016.
Nu Mark LLC, IPR2016-01297, Ex. 1016 U.S. Pat. No. 4,797,692 ("Ims"), Jun. 28, 2016.
Nu Mark LLC, IPR2016-01297, Ex. 1017 U.S. Pat. No. 3,200,819 ("Gilbert"), Jun. 28, 2016.
Nu Mark LLC, IPR2016-01297, Ex. 1018 U.S. Appl. No. 2006/0093977 A1 ("Pellizzari I"), Jun. 28, 2016.
Nu Mark LLC, IPR2016-01297, Ex. 1019 U.S. Pat. No. 7,059,307 ("Pellizzari II"), Jun. 28, 2016.
Nu Mark LLC, IPR2016-01297, Ex. 1020 U.S. Pat. No. 6,501,052 ("Cox II"), Jun. 28, 2016.
Nu Mark LLC, IPR2016-01297, Ex. 1021 U.S. Pat. No. 6,234,167 ("Cox"), Jun. 28, 2016.
Nu Mark LLC, IPR2016-01297, Ex. 1022 U.S. Pat. No. 5,666,977 ("Higgins"), Jun. 28, 2016.
Nu Mark LLC, IPR2016-01297, Ex. 1023 European Patent Application No. 0358114 A2 ("Brooks 114"), Jun. 28, 2016.
Nu Mark LLC, IPR2016-01297, Ex.1024 U.S. Pat. No. 3,203,025 ("Schreur"), Jun. 28, 2016.
Nu Mark LLC, IPR2016-01297, Ex. 1025 U.S. Patent Publication No. 2001/0026788 ("Piskorz"), Jun. 28, 2016.
Nu Mark LLC, IPR2016-01297, Ex. 1026 European Patent Application No. EP0845220 B1 ("Susa"), Jun. 28, 2016.
Nu Mark LLC, IPR2016-01297, Ex. 1027 U.S. Pat. No. 5,745,985 ("Ghosh"), Jun. 28, 2016.
Nu Mark LLC, IPR2016-01297, Ex. 1028 U.S. Pat. No. 4,676,237 ("Wood"), Jun. 28, 2016.
Nu Mark LLC, IPR2016-01297, Ex. 1029 U.S. Pat. No. 4,945,448 ("Bremenour"), Jun. 28, 2016.
Nu Mark LLC, IPR2016-01297, Ex.1030 Certified Translation of Chinese Utility Model Publication No. CN1233436A ("Hongbin"), Jun. 28, 2016.
Nu Mark LLC, IPR2016-01297, Ex. 1031 Decision—Denying Institution of Inter Partes Review, Case No. IPR2015-01302 ("726 Decision"), Jun. 28, 2016.
Nu Mark LLC, IPR2016-01297, Ex. 1032 U.S. Pat. No. 6,102,036 ("Slutsky"), Jun. 28, 2016.
Nu Mark LLC, IPR2016-01297, Ex. 1033 Decision—Institution of Inter Partes Review, Case No. IPR2014-00424 ("148 Decision"), Jun. 28, 2016.
Nu Mark LLC, IPR2016-01297, Ex. 1034 U.S. Pat. No. 6,491,233 ("Nichols"), Jun. 28, 2016.
Nu Mark LLC, IPR2016-01299, Paper 1, Petition for Inter Partes Review of U.S. Pat. No. 8,393,331, Jun. 28, 2016.
Nu Mark LLC, IPR2016-01299, Ex. 1001 U.S. Pat. No. 8,393,331 ("the 331 Patent"), Jun. 28, 2016.
Nu Mark LLC, IPR2016-01299, Ex. 1002 File History for U.S. Pat. No. 8,393,331, Jun. 28, 2016.
Nu Mark LLC, IPR2016-01299, Ex. 1003 Declaration of John M. Collins, Ph.D. ("Collins Decl."), Jun. 28, 2016.
Nu Mark LLC, IPR2016-01299, Ex. 1004 U.S. Pat. No. 6,155,268 ("Takeuchi"), Jun. 28, 2016.
Nu Mark LLC, IPR2016-01299, Ex. 1005 U.S. Pat. No. 2,057,353 ("Whittemore"), Jun. 28, 2016.
Nu Mark LLC, IPR2016-01299, Ex. 1006 U.S. Pat. No. 4,947,874 ("Brooks 874"), Jun. 28, 2016.
Nu Mark LLC, IPR2016-01299, Ex. 1007 Decision—Institution of Inter Partes Review, Case No. IPR2014-01289 ("331 Decision"), Jun. 28, 2016.
Nu Mark LLC, IPR2016-01299, Ex. 1008 Order to Terminate Proceedings, Case No. IPR2014-01300, Jun. 28, 2016.
Nu Mark LLC, IPR2016-01299, Ex. 1009 U.S. Pat. No. 5,743,251 ("Howell"), Jun. 28, 2016.
Nu Mark LLC, IPR2016-01299, Ex. 1010 U.S. Pat. No. 6,598,607 ("Adiga"), Jun. 28, 2016.
Nu Mark LLC, IPR2016-01299, Ex. 1011 U.S. Pat. No. 5,894,841 ("Voges"), Jun. 28, 2016.
Nu Mark LLC, IPR2016-01299, Ex. 1012 U.S. Pat. No. 4,990,939 ("Sekiya"), Jun. 28, 2016.
Nu Mark LLC, IPR2016-01299, Ex. 1013 U.S. Pat. No. 4,771,295 ("Baker"), Jun. 28, 2016.
Nu Mark LLC, IPR2016-01299, Ex. 1014 U.S. Pat. No. 5,703,633 ("Gehrer"), Jun. 28, 2016.
Nu Mark LLC, IPR2016-01299, Ex. 1015 U.S. Pat. No. 5,497,791 ("Bowen"), Jun. 28, 2016.
Nu Mark LLC, IPR2016-01299, Ex. 1016 U.S. Pat. No. 4,797,692 ("Ims"), Jun. 28, 2016.
Nu Mark LLC, IPR2016-01299, Ex. 1017 Thermal Ink-Jet Print Cartridge Designers Guide ("Ink-Jet Guide"), Jun. 28, 2016.
Nu Mark LLC, IPR2016-01299, Ex. 1018 U.S. Patent Pub. No. 2006/0093977 ("Pellizzari I"), Jun. 28, 2016.
Nu Mark LLC, IPR2016-01299, Ex. 1019 U.S. Pat. No. 7,059,307 ("Pellizzari II"), Jun. 28, 2016.
Nu Mark LLC, IPR2016-01299, Ex. 1020 U.S. Pat. No. 3,502,588 ("Winberg"), Jun. 28, 2016.
Nu Mark LLC, IPR2016-01299, Ex. 1021 U.S. Pat. No. 6,234,167 ("Cox"), Jun. 28, 2016.

(56) References Cited

OTHER PUBLICATIONS

Nu Mark LLC, IPR2016-01299, Ex. 1022 U.S. Pat. No. 5,666,977 ("Higgins"), Jun. 28, 2016.
Nu Mark LLC, IPR2016-01299, Ex. 1023 European Patent Application No. 0358114 A2 ("Brooks 114"), Jun. 28, 2016.
Nu Mark LLC, IPR2016-01299, Ex. 1024 U.S. Pat. No. 7,284,424 ("Kanke"), Jun. 28, 2016.
Nu Mark LLC, IPR2016-01299, Ex. 1025 U.S. Pat. No. 5,224,265 ("Dux"), Jun. 28, 2016.
Nu Mark LLC, IPR2016-01299, Ex. 1026 U.S. Pat. No. 6,620,659 ("Emmma"), Jun. 28, 2016.
Nu Mark LLC, IPR2016-01299, Ex. 1027 U.S. Pat. No. 5,745,985 ("Ghosh"), Jun. 28, 2016.
Nu Mark LLC, IPR2016-01299, Ex. 1028 U.S. Pat. No. 4,676,237 ("Wood"), Jun. 28, 2016.
Nu Mark LLC, IPR2016-01299, Ex. 1029 U.S. Pat. No. 4,945,448 ("Bremenour"), Jun. 28, 2016.
Nu Mark LLC, IPR2016-01299, Ex. 1030 Certified Translation of Chinese Utility Model Publication No. CN 1233436A ("Hongbin"), Jun. 28, 2016.
Nu Mark LLC, IPR2016-01299, Ex. 1031 U.S. Pat. No. 6,196,218 ("Voges 218"), Jun. 28, 2016.
Nu Mark LLC, IPR2016-01299, Ex. 1032 U.S. Pat. No. 3,747,120 ("Stemme"), Jun. 28, 2016.
Nu Mark LLC, IPR2016-01299, Ex. 1033 Decision—Institution of Inter Partes Review—IPR2014-00424 ("148 Decision"), Jun. 28, 2016.
Nu Mark LLC, IPR2016-01299, Ex. 1034 U.S. Pat. No. 3,200,819 ("Gilbert"), Jun. 28, 2016.
Nu Mark LLC, IPR2016-01299, Ex. 1035 U.S. Pat. No. 6,501,052 ("Cox II"), Jun. 28, 2016.
Nu Mark LLC, IPR2016-01299, Ex. 1036 U.S. Pat. No. 6,491,233 ("Nichols"), Jun. 28, 2016.
Nu Mark LLC, IPR2016-01438, Paper 1, Petition for Inter Partes Review of U.S. Pat. No. 8,393,331, Jul. 14, 2016.
Nu Mark LLC, PR2016-01438, Ex. 1101 U.S. Pat. No. 8,393,331 (the "331 Patent"), Jul. 14, 2016.
Nu Mark LLC, PR2016-01438, Ex. 1102 File History for U.S. Pat. No. 8,393,331, Jul. 14, 2016.
Nu Mark LLC, PR2016-01438, Ex. 1103 Declaration of John M. Collins, Ph.D., Jul. 14, 2016.
Nu Mark LLC, PR2016-01438, Ex. 1104 Curriculum Vitae of Dr. John M. Collins, Jul. 14, 2016.
Nu Mark LLC, PR2016-01438, Ex. 1105 U.S. Pat. App. Pub. No. 2007/0267031 A1 ("Hon 031"), Jul. 14, 2016.
Nu Mark LLC, PR2016-01438, Ex .1106 File History for App. No. 12/944,123, Jul. 14, 2016.
Nu Mark LLC, PR2016-01438, Ex. 1107 Substitute Specification filed in U.S. Appl. No. 12/944,123, Jul. 14, 2016.
Nu Mark LLC, PR2016-01438, Ex. 1108 File History for U.S. Appl. No. 10/587,707 (issued as U.S. Pat. No. 7,832,410), Jul. 14, 2016.
Nu Mark LLC, PR2016-01438, Ex. 1109 Certified Translation of CN 20040031182, Jul. 14, 2016.
Nu Mark LLC, PR2016-01438, Ex. 1110 Decision Instituting Inter Partes Review—IPR2014-01289, Jul. 14, 2016.
Nu Mark LLC, PR2016-01438, Ex. 1111 Claim Construction Order, *Fontem Ventures B. V. et al.* v. *NJOY, Inc et al.*, Civil Action No. 2:14-cv-1645 (C.D. Cal.), Jan. 29, 2015, Jul. 14, 2016.
Nu Mark LLC, PR2016-01438, Ex. 1112 U.S. Pat. No. 7,832,410 (the "410 Patent"), Jul. 14, 2016.
Nu Mark LLC, PR2016-01438, Ex. 1113 U.S. Pat. No. 8,689,805 (the "805 Patent"), Jul. 14, 2016.
Nu Mark LLC, PR2016-01438, Ex. 1114 File History for U.S. Appl. No. 13/426,817 (issued as U.S. Pat. No. 8,689,805), Jul. 14, 2016.
Nu Mark LLC, PR2016-01438, Ex. 1115 EP1736065 AI, Jul. 14, 2016.
Nu Mark LLC, PR2016-01438, Ex. 1116 Complaint, *Fontem Ventures B. V., et al.* v. *Nu Mark LLC*, Case No. 2:16-cv-02291 (excerpt), Jul. 14, 2016.
Nu Mark LLC, PR2016-01438, Ex. 1117 Certified Translation of WO 2005/099494, Jul. 14, 2016.
Nu Mark LLC, PR2016-01438, Ex. 1118 WO 2005/099494 Chinese version with English abstract (face), Jul. 14, 2016.
Nu Mark LLC, IPR2016-01664, Paper 1, Petition for Inter Partes Review of U.S. Pat. No. 9,326,549, Aug. 22, 2016.
Nu Mark LLC, IPR2016-01664, Ex. 1001 U.S. Pat. No. 9,326,549 (the "549 Patent"), Aug. 22, 2016.
Nu Mark LLC, IPR2016-01664, Ex.1002 File History for U.S. Pat. No. 9,326,549, Aug. 22, 2016.
Nu Mark LLC, IPR2016-01664, Ex. 1003 Declaration of John M. Collins, Ph.D., Aug. 22, 2016.
Nu Mark LLC, IPR2016-01664, Ex.1004 Curriculum Vitae of Dr. John M. Collins, Aug. 22, 2016.
Nu Mark LLC, IPR2016-01664, Ex.1005 U.S. Pat. App. Pub. No. 2007/0267031 A1 ("Hon 031"), Aug. 22, 2016.
Nu Mark LLC, IPR2016-01664, Ex.1006 File History for U.S. Appl. No. 12/944,123 (issued as U.S. Pat. No. 8,393,331), Aug. 22, 2016.
Nu Mark LLC, IPR2016-01664, Ex.1007 Substitute Specification filed in U.S. Appl. No. 12/944,123 (issued as U.S. Pat. No. 8,393,331), Aug. 22, 2016.
Nu Mark LLC, IPR2016-01664, Ex.1008 File History for U.S. Appl. No. 10/587,707 (issued as U.S. Pat. No. 7,832,410), Aug. 22, 2016.
Nu Mark LLC, IPR2016-01664, Ex. 1009 Certified Translation of CN 20040031182, Aug. 22, 2016.
Nu Mark LLC, IPR2016-01664, Ex.1010 Decision Instituting Inter Partes Review—IPR2014-01289, Aug. 22, 2016.
Nu Mark LLC, IPR2016-01664, Ex.1011 Claim Construction Order, *Fontem Ventures B.V., et al.* v. *NJOY, Inc., et al.*, Case No. 2:14-cv-01645, Jan. 29, 2015 (Dkt. 65), Aug. 22, 2016.
Nu Mark LLC, IPR2016-01664, Ex.1012 U.S. Pat. No. 7,832,410 (the "410 Patent"), Aug. 22, 2016.
Nu Mark LLC, IPR2016-01664, Ex.1013 U.S. Pat. No. 8,689,805 (the "805 Patent"), Aug. 22, 2016.
Nu Mark LLC, IPR2016-01664, Ex.1014 File History for U.S. Appl. No. 13/426,817 (issued as U.S. Pat. No. 8,689,805), Aug. 22, 2016.
Nu Mark LLC, IPR2016-01664, Ex. 1015 European Patent No. 1736065 A1 to Hon, Aug. 22, 2016.
Nu Mark LLC, IPR2016-01664, Ex.1016 Complaint, *Fontem Ventures B.V., et al.* v. *Nu Mark LLC*, Case No. 2:16-cv-04537, Jun. 22, 2016 (Dkt. 1), Aug. 22, 2016.
Nu Mark LLC, IPR2016-01664, Ex. 1017 Certified Translation of WO 2005/099494, Aug. 22, 2016.
R.J. Reynolds Vapor Company, Answer to Complaint in *Fontem Holdings B.V.* v. *R.J. Reynolds Vapor Company*, 16-CV-2286, Dkt. 027, Jun. 27, 2016.
R.J. Reynold Vapor Company, Answer to Complaint in *Fontem Holdings B.V.* v. *R.J. Reynolds Vapor Company*, 16-CV-3049, Dkt. 028, Jul. 25, 2016.
R.J. Reynolds Vapor Company, First Amended Answer to Complaint in *Fontem Holdings B.V.* v. *R.J. Reynolds Vapor Company*, 16-CV-2286, Dkt. 033, Jul. 25, 2016.
R.J. Reynolds Vapor Company, Preliminary Invalidity Contentions served in *Fontem Ventures B.V.* v. *R.J. Reynolds Vapor Company*, U.S. District Court for the Middle District of North Carolina, 16-cv-01255, Mar. 15, 2017.
R.J. Reynolds Vapor Company, Preliminary Invalidity Contentions, Exhibit B ('628 patent), 16-cv-01255, Mar. 15, 2017.
R.J. Reynolds Vapor Company, Preliminary Invalidity Contentions, Exhibit C ('726 patent), 16-cv-01255, Mar. 15, 2017.
R.J. Reynolds Vapor Company, Preliminary Invalidity Contentions, Exhibit F ('549 patent), 16-cv-01255, Mar. 15, 2017.
R.J. Reynolds Vapor Company, Preliminary Invalidity Contentions for 17-cv-0175, Jul. 31, 2017.
R.J. Reynolds Vapor Company, Preliminary Invalidity Contentions, Exhibit F (U.S. Pat. No. 8,393,331), 17-cv-0175, Jul. 31, 2017.
R.J. Reynolds Vapor Company, Final Invalidity Contentions served in *Fontem Holdings B.V.* v. *R.J. Reynolds Vapor Company*, U.S. District Court for the Middle District of North Carolina, Case No.

(56) References Cited

OTHER PUBLICATIONS 16-cv-1255 and consolidated cases (relating to patent U.S. Pat. Nos. 8,365,742, 8,490,628, 8,893,726, 8,899,239, 8,326,548, 8,326,549, and 9,370,205), May 7, 2018.
R.J. Reynolds Vapor Company, Final Invalidity Elections served in *Fontem Holdings B.V. v. R.J. Reynolds Vapor Company*, U.S. District Court for the Middle District of North Carolina, Case No. 16-cv-1255 and consolidated cases (relating to patent U.S. Pat. Nos. 8,365,742, 8,490,628, 8,893,726, 8,899,239, 8,326,548, 8,326,549, and 9,370,205), May 7, 2018.
R.J. Reynolds Vapor Company, Final Invalidity Contentions, 16-cv-1255 and consolidated cases, Amended Exhibit B (U.S. Pat. No. 8,490,628), May 7, 2018.
R.J. Reynolds Vapor Company, Final Invalidity Contentions, 16-cv-1255 and consolidated cases, Amended Exhibit C (U.S. Pat. No. 8,893,726), May 7, 2018.
R.J. Reynolds Vapor Company, Final Invalidity Contentions, 16-cv-1255 and consolidated cases, Amended Exhibit F (U.S. Pat. No. 8,326,549), May 7, 2018.
R.J. Reynolds Vapor Company, Final Invalidity Contentions served in *Fontem Holdings B.V. v. R.J. Reynolds Vapor Company*, U.S. District Court for the Middle District of North Carolina, Case No. 16-cv-1255 and consolidated cases (relating to patent U.S. Pat. Nos. 8,375,957, 8,863,752 9,326,550, 9,326,551, 9,339,062, 8,393,331, 9,364,027, and 9,456,632), May 7, 2018.
R.J. Reynolds Vapor Company, Final Invalidity Elections served in *Fontem Holdings B.V. v. R.J. Reynolds Vapor Company*, U.S. District Court for the Middle District of North Carolina, Case No. 16-cv-1255 and consolidated cases (relating to patent U.S. Pat. Nos. 8,375,957, 8,863,752 9,326,550, 9,326,551, 9,339,062, 8,393,331, 9,364,027, and 9,456,632), May 7, 2018.
R.J. Reynolds Vapor Company, Final Invalidity Contentions, 16-cv-1255 and consolidated cases, Amended Exhibit F (U.S. Pat. No. 8,393,331), May 7, 2018.
R.J. Reynolds Vapor Company, IPR2016-01270, Paper 2, Petition for Inter Partes Review of U.S. Pat. No. 8,893,726, Jul. 2, 2016.
R.J. Reynolds Vapor Company, IPR2016-01270, Ex. 1001 U.S. Pat. No. 8,893,726 ("'726 Patent"), Jul. 2, 2016.
R.J. Reynolds Vapor Company, IPR2016-01270, Ex. 1002 '726 Patent File History, Non-Final Rejection (Aug. 16, 2013) ("Non-Final Rejection"), Jul. 2, 2016.
R.J. Reynolds Vapor Company, IPR2016-01270, Ex. 1003 '726 Patent File History, Amendment (Oct. 8, 2013) ("Amendment"), Jul. 2, 2016.
R.J. Reynolds Vapor Company, IPR2016-01270, Ex. 1004 '726 Patent File History, Notice of Allowance (Aug. 18, 2014), Jul. 2, 2016.
R.J. Reynolds Vapor Company, IPR2016-01270, Ex. 1005 *NJOY, Inc. v. Fontem Holdings 1 B.V.*, IPR2015-01302 (PTAB, filed May 29, 2015), Paper No. 15 ("Prior Decision"), Jul. 2, 2016.
R.J. Reynolds Vapor Company, IPR2016-01270, Ex. 1006 U.S. Pat. No. 4,947,874 ("Brooks"), Jul. 2, 2016.
R.J. Reynolds Vapor Company, IPR2016-01270, Ex. 1007 U.S. Pat. No. 5,944,025 ("Cook"), Jul. 2, 2016.
R.J. Reynolds Vapor Company, IPR2016-01270, Ex. 1008 U.S. Pat. No. 6,155,268 ("Takeuchi"), Jul. 2, 2016.
R.J. Reynolds Vapor Company, IPR2016-01270, Ex. 1009 Declaration of Robert Sturges, Ph.D. ("Sturges Decl."), Jul. 2, 2016.
R.J. Reynolds Vapor Company, IPR2016-01270, Ex. 1010 *NJOY, Inc. v. Fontem Holdings 1 B.V.*, IPR2015-01302 (PTAB, filed May 29, 2015), Paper No. 2 ("NJOY Petition"), Jul. 2, 2016.
R.J. Reynolds Vapor Company, IPR2016-01270, Ex. 1011 *NJOY, Inc. v. Fontem Holdings 1 B.V.*, IPR2015-01302 (PTAB, filed May 29, 2015), Paper No. 6 ("Patent Owner Preliminary Response"), Jul. 2, 2016.
R.J. Reynolds Vapor Company, IPR2016-01270, Ex. 1012 U.S. Pat. No. 5,703,633 ("Gehrer"), Jul. 2, 2016.
R.J. Reynolds Vapor Company, IPR2016-01527, Paper 1, Petition for Inter Partes Review of U.S. Pat. No. 8,490,628, Aug. 3, 2016.

R.J. Reynolds Vapor Company, IPR2016-01527, Ex. 1001 U.S. Pat. No. 8,490,628 ("the '628 patent"), Aug. 3, 2016.
R.J. Reynolds Vapor Company, IPR2016-01527, Ex. 1002 The '628 Patent File History, Aug. 3, 2016.
R.J. Reynolds Vapor Company, IPR2016-01527, Ex. 1003 U.S. Pat. No. 6,155,268 ("Takeuchi"), Aug. 3, 2016.
R.J. Reynolds Vapor Company, IPR2016-01527, Ex. 1004 U.S. Pat. No. 2,057,353 ("Whittemore"), Aug. 3, 2016.
R.J. Reynolds Vapor Company, IPR2016-01527, Ex. 1005 U.S. Pat. No. 5,894,841 ("Voges"), Aug. 3, 2016.
R.J. Reynolds Vapor Company, IPR2016-01527, Ex. 1006 U.S. Pat. No. 5,703,633 ("Gehrer"), Aug. 3, 2016.
R.J. Reynolds Vapor Company, IPR2016-01527, Ex. 1007 "Thermal Ink-Jet Print Cartridge Designers Guide" (2nd Edition Hewlett Packard), Aug. 3, 2016.
R.J. Reynolds Vapor Company, IPR2016-01527, Ex. 1008 IPR2014-01300 Paper 8: Decision for Inter Partes Review Institution, Aug. 3, 2016.
R.J. Reynolds Vapor Company, IPR2016-01527, Ex. 1009 IPR2014-01300 Paper 2: Inter Partes Review Petition, Aug. 3, 2016.
R.J. Reynolds Vapor Company, IPR2016-01527, Ex. 1010 Expert Declaration of Robert Sturges, Ph.D. ("Sturges Decl."), Aug. 3, 2016.
R.J. Reynolds Vapor Company, IPR2016-01527, Ex. 1011 U.S. Pat. No. 5,743,251 ("Howell"), Aug. 3, 2016.
R.J. Reynolds Vapor Company, IPR2016-01527, Ex. 1012 U.S. Pat. No. 1,514,682 ("Wilson"), Aug. 3, 2016.
R.J. Reynolds Vapor Company, IPR2016-01527, Ex. 1013 U.S. Pat. No. 4,947,874 ("Brooks"), Aug. 3, 2016.
R.J. Reynolds Vapor Company, IPR2016-01527, Ex. 1014 U.S. Pat. No. 5,745,985 ("Ghosh"), Aug. 3, 2016.
R.J. Reynolds Vapor Company, IPR2016-01527, Ex. 1015 U.S. Pat. No. 4,676,237 ("Wood"), Aug. 3, 2016.
R.J. Reynolds Vapor Company, IPR2016-01527, Ex. 1016 U.S. Pat. No. 4,945,448 ("Bremenour"), Aug. 3, 2016.
R.J. Reynolds Vapor Company, IPR2016-01527, Ex. 1017 U.S. Pat. No. 6,322,269 ("Kaufman"), Aug. 3, 2016.
R.J. Reynolds Vapor Company, IPR2016-01527, Ex. 1018 U.S. Pat. No. 6,722,763 ("Hsu"), Aug. 3, 2016.
R.J. Reynolds Vapor Company, IPR2016-01527, Ex. 1019 U.S. Pat. No. 5,646,666 ("Cowger"), Aug. 3, 2016.
R.J. Reynolds Vapor Company, IPR2016-01527, Ex. 1020 U.S. Pat. No. 7,284,424 ("Kanke"), Aug. 3, 2016.
R.J. Reynolds Vapor Company, IPR2016-01527, Ex. 1021 U.S. Pat. No. 5,224,265 ("Dux"), Aug. 3, 2016.
R.J. Reynolds Vapor Company, IPR2016-01527, Ex. 1022 U.S. Pat. No. 6,620,659 ("Emmma"), Aug. 3, 2016.
R.J. Reynolds Vapor Company, IPR2016-01859, Paper 2, Petition for Inter Partes Review of U.S. Pat. No. 9,326,549, Sep. 23, 2016.
R.J. Reynolds Vapor Company, IPR2016-01859, Ex. 1001 U.S. Pat. No. 9,326,549, Sep. 23, 2016.
R.J. Reynolds Vapor Company, IPR2016-01859, Ex. 1002 '549 Patent File History, Sep. 23, 2016.
R.J. Reynolds Vapor Company, IPR2016-01859, Ex. 1003 U.S. Pat. Pub. No. 2007/0267031 A1 to Lik Hon (issued as U.S. Pat. No. 7,832,410), Sep. 23, 2016.
R.J. Reynolds Vapor Company, IPR2016-01859, Ex. 1004 U.S. Pat. No. 7,832,410, Sep. 23, 2016.
R.J. Reynolds Vapor Company, IPR2016-01859, Ex. 1005 File History for U.S. Pat. No. 7,832,410, Sep. 23, 2016.
R.J. Reynolds Vapor Company, IPR2016-01859, Ex. 1006 Excerpt of File History for U.S. Pat. No. 8,393,331, Sep. 23, 2016.
R.J. Reynolds Vapor Company, IPR2016-01859, Ex. 1007 Substitute Specification filed in U.S. Pat. No. 8,393,331, Sep. 23, 2016.
R.J. Reynolds Vapor Company, IPR2016-01859, Ex. 1008 WO 2005/099494 with English abstract (front page), Sep. 23, 2016.
R.J. Reynolds Vapor Company, IPR2016-01859, Ex. 1009 Certified Translation of WO 2005/099494, Sep. 23, 2016.
R.J. Reynolds Vapor Company, IPR2016-01859, Ex. 1010 Certified Translation of CN 20040031182, Sep. 23, 2016.
R.J. Reynolds Vapor Company, IPR2016-01859, Ex. 1011 U.S. Pat. No. 8,689,805, Sep. 23, 2016.

(56) References Cited

OTHER PUBLICATIONS

R.J. Reynolds Vapor Company, IPR2016-01859, Ex. 1012 Excerpt of File History for U.S. Pat. No. 8,689,805, Sep. 23, 2016.
R.J. Reynolds Vapor Company, IPR2016-01859, Ex. 1013 *NJOY, Inc.* v. *Fontem Holdings 1 B.V.*, IPR2014-01289 (PTAB, filed Aug. 14, 2014), Paper No. 8, Sep. 23, 2016.
R.J. Reynolds Vapor Company, IPR2016-01859, Ex. 1014 *NJOY, Inc.* v. *Fontem Holdings 1 B.V.*, IPR2014-01300 (PTAB, filed Aug. 15, 2014), Paper No. 8, Sep. 23, 2016.
R.J. Reynolds Vapor Company, IPR2016-01859, Ex. 1015 *NJOY, Inc.* v. *Fontem Holdings 1 B.V.*, IPR2015-01302 (PTAB, filed May 29, 2015), Paper No. 15, Sep. 23, 2016.
R.J. Reynolds Vapor Company, IPR2016-01859, Ex. 1016 Complaint, *Fontem Ventures B.V. et al.* v. *R.J. Reynolds Vapor Company*, No. 2:16-cv-03049 (C.D. Cal., filed May 3, 2016) (excerpts), Sep. 23, 2016.
R.J. Reynolds Vapor Company, IPR2016-01859, Ex. 1017 Declaration of Robert Sturges, Ph.D., Sep. 23, 2016.
R.J. Reynolds Vapor Company, IPR2016-01859, Ex. 1018 EP 1736065 A1, Sep. 23, 2016.
R.J. Reynolds Vapor Company, IPR2016-01859, Ex. 1019 Claim Construction Order, *Fontem Ventures B.V., et al.* v. *NJOY, Inc.*, et al., Case No. 2:14-cv-01645, Jan. 29, 2015 (Dkt. 65), Sep. 23, 2016.
R.J. Reynolds Vapor Company, IPR2017-01117, Paper 2, Petition for Inter Partes Review of U.S. Pat. No. 8,893,726, Apr. 4, 2017.
R.J. Reynolds Vapor Company, IPR2017-01117, Ex. 1001—U.S. Pat. No. 8,893,726, Apr. 4, 2017.
R.J. Reynolds Vapor Company, IPR2017-01117, Ex. 1002—726 Patent File History, Non-Final Rejection (Aug. 16, 2013), Apr. 4, 2017.
R.J. Reynolds Vapor Company, IPR2017-01117, Ex. 1003—726 Patent File History, Amendment (Oct. 8, 2013), Apr. 4, 2017.
R.J. Reynolds Vapor Company, IPR2017-01117, Ex. 1004—726 Patent File History, Notice of Allowance (Aug. 18, 2014), Apr. 4, 2017.
R.J. Reynolds Vapor Company, IPR2017-01117, Ex. 1005—*NJOY, Inc.* v. *Fontem Holdings 1 B.V.*, IPR2015-01302 (PTAB, filed May 29, 2015), Paper No. 15, Apr. 4, 2017.
R.J. Reynolds Vapor Company, IPR2017-01117, Ex. 1006—*R.J. Reynolds Vapor Company* v. *Fontem Holdings 1 B.V.*, IPR2016-01270 (PTAB, filed Jul. 2, 2016), Paper No. 11, Apr. 4, 2017.
R.J. Reynolds Vapor Company, IPR2017-01117, Ex. 1007—U.S. Patent No. 5,144,962, Apr. 4, 2017.
R.J. Reynolds Vapor Company, IPR2017-01117, Ex. 1008—U.S. Pat. No. 4,981,522, Apr. 4, 2017.
R.J. Reynolds Vapor Company, IPR2017-01117, Ex. 1009—Declaration of Robert Sturges, Ph.D., Apr. 4, 2017.
R.J. Reynolds Vapor Company, IPR2017-01117, Ex. 1010—*NJOY, Inc.* v. *Fontem Holdings 1 B.V.*, IPR2015-01302 (PTAB, filed May 29, 2015), Paper No. 6, Apr. 4, 2017.
R.J. Reynolds Vapor Company, IPR2017-01117, Ex. 1011—U.S. Pat. No. 5,894,841, Apr. 4, 2017.
R.J. Reynolds Vapor Company, IPR2017-01117, Ex. 1012—U.S. Pat. No. 6,155,268, Apr. 4, 2017.
R.J. Reynolds Vapor Company, IPR2017-01117, Ex. 1013—U.S. Pat. No. 5,129,409.
R.J. Reynolds Vapor Company, IPR2017-01117, Ex. 1014—U.S. Pat. No. 1,016,844.
R.J. Reynolds Vapor Company, IPR2017-01117, Ex. 1015—U.S. Pat. No. 3,385,303.
R.J. Reynolds Vapor Company, IPR2017-01117, Ex. 1016—U.S. Pat. No. 3,428,053.
R.J. Reynolds Vapor Company, IPR2017-01117, Ex. 1017—U.S. Pat. No. 3,860,012.
R.J. Reynolds Vapor Company, IPR2017-01117, Ex. 1018—U.S. Pat. No. 4,270,552.
R.J. Reynolds Vapor Company, IPR2017-01117, Ex. 1019—U.S. Pat. No. 4,589,428.
R.J. Reynolds Vapor Company, IPR2017-01117, Ex. 1020—U.S. Pat. No. 5,745,985.
R.J. Reynolds Vapor Company, IPR2017-01117, Ex. 1021—U.S. Pat. No. 4,208,005.
R.J. Reynolds Vapor Company, IPR2017-01117, Ex. 1022—Excerpt from James W. Dally, Packaging of Electronic Systems: A Mechanical Engineering Approach (1990).
R.J. Reynolds Vapor Company, IPR2017-01118, Paper 2, Petition for Inter Partes Review of U.S. Pat. No. 8,490,628, Apr. 3, 2017.
R.J. Reynolds Vapor Company, IPR2017-01118 Exhibit-1001—U.S. Pat. No. 8,490,628, Apr. 3, 2017.
R.J. Reynolds Vapor Company, IPR2017-01118 Exhibit-1002—Expert Declaration of Robert Sturges, Ph.D., Apr. 3, 2017.
R.J. Reynolds Vapor Company, IPR2017-01118 Exhibit-1003—U.S. Pat. No. 6,155,268, Apr. 3, 2017.
R.J. Reynolds Vapor Company, IPR2017-01118 Exhibit-1004—U.S. Pat. No. 2,057,353, Apr. 3, 2017.
R.J. Reynolds Vapor Company, IPR2017-01118 Exhibit-1005—The '628 Patent File History, Apr. 3, 2017.
R.J. Reynolds Vapor Company, IPR2017-01118 Exhibit-1006—IPR2016-01527 Paper 10: Decision for Inter Partes Review Institution, Apr. 3, 2017.
R.J. Reynolds Vapor Company, IPR2017-01118 Exhibit-1007—IPR2016-01283 Paper 12: Decision for Inter Partes Review Institution, Apr. 3, 2017.
R.J. Reynolds Vapor Company, IPR2017-01118 Exhibit-1008—IPR2016-01285 Paper 10: Decision for Inter Partes Review Institution, Apr. 3, 2017.
R.J. Reynolds Vapor Company, IPR2017-01118 Exhibit-1009—IPR2014-01300 Paper 8: Decision for Inter Partes Review Institution, Apr. 3, 2017.
R.J. Reynolds Vapor Company, IPR2017-01118 Exhibit-1010—U.S. Pat. No. 5,743,251, Apr. 3, 2017.
R.J. Reynolds Vapor Company, IPR2017-01118 Exhibit-1011—U.S. Pat. No. 1,514,682, Apr. 3, 2017.
R.J. Reynolds Vapor Company, IPR2017-01118 Exhibit-1012—U.S. Pat. No. 7,284,424, Apr. 3, 2017.
R.J. Reynolds Vapor Company, IPR2017-01118 Exhibit-1013—U.S. Pat. No. 4,947,874, Apr. 3, 2017.
R.J. Reynolds Vapor Company, IPR2017-01118 Exhibit-1014—U.S. Pat. No. 5,745,985, Apr. 3, 2017.
R.J. Reynolds Vapor Company, IPR2017-01118 Exhibit-1015—U.S. Pat. No. 4,208,005, Apr. 3, 2017.
R.J. Reynolds Vapor Company, IPR2017-01118 Exhibit-1016—U.S. Pat. No. 4,945,448, Apr. 3, 2017.
R.J. Reynolds Vapor Company, IPR2017-01118 Exhibit-1017—U.S. Pat. No. 5,144,962, Apr. 3, 2017.
R.J. Reynolds Vapor Company, IPR2017-01118 Exhibit-1018—Engineers, Eugene A. Avallone et al., published 1978, p. 15-6, Apr. 3, 2017.
R.J. Reynolds Vapor Company, IPR2017-01118 Exhibit-1019—Excerpts from James W. Dally, Packaging of Electronic Systems: A Mechanical Engineering Approach (1990), Apr. 3, 2017.
R.J. Reynolds Vapor Company, IPR2017-01118 Exhibit-1020—U.S. Pat. No. 6,598,607, Apr. 3, 2017.
R.J. Reynolds Vapor Company, IPR2017-01118 Exhibit-1021—U.S. Pat. No. 4,793,365, Apr. 3, 2017.
R.J. Reynolds Vapor Company, IPR2017-01118 Exhibit-1022—U.S. Pat. No. 5,203,355, Apr. 3, 2017.
R.J. Reynolds Vapor Company, IPR2017-01118 Exhibit-1023—U.S. Pat. No. 2,472,282, Apr. 3, 2017.
R.J. Reynolds Vapor Company, IPR2017-01118 Exhibit-1024—U.S. Pat. No. 2,032,695, Apr. 3, 2017.
R.J. Reynolds Vapor Company, IPR2017-01118 Exhibit-1025—Wire, Merriam-Webster's Collegiate Dictionary (10th ed. 2002), Apr. 3, 2017.
R.J. Reynolds Vapor Company, IPR2017-01118 Exhibit-1026—Declaration of James Donnelly, Apr. 3, 2017.
R.J. Reynolds Vapor Company, IPR2017-01119, Paper 2, Petition for Inter Partes Review of U.S. Pat. No. 8,490,628, Apr. 4, 2017.
R.J. Reynolds Vapor Company, IPR2017-01119, Ex. 1001—U.S. Pat. No. 8,490,628, Apr. 4, 2017.
R.J. Reynolds Vapor Company, IPR2017-01119, Ex. 1002—Certified translation of CN 20040031182, Apr. 4, 2017.

(56) References Cited

OTHER PUBLICATIONS

R.J. Reynolds Vapor Company, IPR2017-01119, Ex. 1003—U.S. Pat. Pub. No. 2007/0267031 A1 to Lik Hon (issued as U.S. Pat. No. 7,832,410), Apr. 4, 2017.
R.J. Reynolds Vapor Company, IPR2017-01119, Ex. 1004—U.S. Pat. No. 7,832,410, Apr. 4, 2017.
R.J. Reynolds Vapor Company, IPR2017-01119, Ex. 1005—File History for U.S. Appl. No. 10/587,707 (issued as U.S. Pat. No. 7,832,410), Apr. 4, 2017.
R.J. Reynolds Vapor Company, IPR2017-01119, Ex. 1006—Excerpt of File History for U.S. Appl. No. 12/944,123 (issued U.S. Pat. No. 8,393,331), Apr. 4, 2017.
R.J. Reynolds Vapor Company, IPR2017-01119, Ex. 1007—Substitute Specification filed in App. No. 12/944,123 (issued as U.S. Pat. No. 8,393,331), Apr. 4, 2017.
R.J. Reynolds Vapor Company, IPR2017-01119, Ex. 1008—Declaration of Robert Sturges, Ph.D., Apr. 4, 2017.
R.J. Reynolds Vapor Company, IPR2017-01119, Ex. 1009—U.S. Pat. No. 8,393,331, Apr. 4, 2017.
R.J. Reynolds Vapor Company, IPR2017-01119, Ex. 1010—IPR2016-01283 Paper 12: Institution Decision for Inter Partes Review, Apr. 4, 2017.
R.J. Reynolds Vapor Company, IPR2017-01119, Ex. 1011—U.S. Pat. No. 8,689,805, Apr. 4, 2017.
R.J. Reynolds Vapor Company, IPR2017-01119, Ex. 1012—File History for U.S. Appl. No. 13/426,817 (issued as 8,689,805), Apr. 4, 2017.
R.J. Reynolds Vapor Company, IPR2017-01119, Ex. 1013—IPR2016-01859 Paper 8: Institution Decision for Inter Partes Review, Apr. 4, 2017.
R.J. Reynolds Vapor Company, IPR2017-01119, Ex. 1014—IPR2014-01300 Paper 8: Institution Decision for Inter Partes Review, Apr. 4, 2017.
R.J. Reynolds Vapor Company, IPR2017-01119, Ex. 1015—Certified Translation of WO 2005/099494, Apr. 4, 2017.
R.J. Reynolds Vapor Company, IPR2017-01180, Paper 2, Petition for Inter Partes Review of U.S. Pat. No. 8,893,726, Apr. 4, 2017.
R.J. Reynolds Vapor Company, IPR2017-01180, Ex. 1001—U.S. Pat. No. 8,893,726, Apr. 4, 2017.
R.J. Reynolds Vapor Company, IPR2017-01180, Ex. 1002—Certified translation of CN 20040031182, Apr. 4, 2017.
R.J. Reynolds Vapor Company, IPR2017-01180, Ex. 1003—U.S. Pat. Pub. No. 2007/0267031 A1 to Lik Hon (issued as U.S. Pat. No. 7,832,410), Apr. 4, 2017.
R.J. Reynolds Vapor Company, IPR2017-01180, Ex. 1004—U.S. Pat. No. 7,832,410, Apr. 4, 2017.
R.J. Reynolds Vapor Company, IPR2017-01180, Ex. 1005—File History for U.S. Appl. No. 10/587,707 (issued as U.S. Pat. No. 7,832,410), Apr. 4, 2017.
R.J. Reynolds Vapor Company, IPR2017-01180, Ex. 1006—Excerpt of File History for U.S. Appl. No. 12/944,123 (issued U.S. Pat. No. 8,393,331), Apr. 4, 2017.
R.J. Reynolds Vapor Company, IPR2017-01180, Ex. 1007—Substitute Specification filed in U.S. Appl. No. 12/944,123 (issued as U.S. Pat. No. 8,393,331), Apr. 4, 2017.
R.J. Reynolds Vapor Company, IPR2017-01180, Ex. 1008—Declaration of Robert Sturges, Ph.D., Apr. 4, 2017.
R.J. Reynolds Vapor Company, IPR2017-01180, Ex. 1009—U.S. Pat. No. 8,393,331, Apr. 4, 2017.
R.J. Reynolds Vapor Company, IPR2017-01180, Ex. 1010—IPR2016-01288 Paper 20: Termination Dismissing the Petitions, Apr. 4, 2017.
R.J. Reynolds Vapor Company, IPR2017-01180, Ex. 1011—U.S. Pat. No. 8,689,805, Apr. 4, 2017.
R.J. Reynolds Vapor Company, IPR2017-01180, Ex. 1012—File History for U.S. Appl. No. 13/426,817 (issued as 8,689,805), Apr. 4, 2017.
R.J. Reynolds Vapor Company, IPR2017-01180, Ex. 1013—IPR2016-01859 Paper 8: Institution Decision for Inter Partes Review, Apr. 4, 2017.
R.J. Reynolds Vapor Company, IPR2017-01180, Ex. 1015—Certified Translation of WO 2005/099494, Apr. 4, 2017.
R.J. Reynolds Vapor Company, IPR2017-01318, Paper 2, Petition for Inter Partes Review of U.S. Pat. No. 9,326,549, May 1, 2017.
R.J. Reynolds Vapor Company, IPR2017-01318, Exhibit 1001—U.S. Pat. No. 9,326,549, May 1, 2017.
R.J. Reynolds Vapor Company, IPR2017-01318, Exhibit 1002—Certified translation of CN20040031182, May 1, 2017.
R.J. Reynolds Vapor Company, IPR2017-01318, Exhibit 1003—U.S. Pat. Pub. No. 2007/0267031 to Lik Hon, (issued as U.S. Pat. No. 7,832,410), May 1, 2017.
R.J. Reynolds Vapor Company, IPR2017-01318, Exhibit 1004—U.S. Pat. No. 7,832,410, May 1, 2017.
R.J. Reynolds Vapor Company, IPR2017-01318, Exhibit 1005—File History for U.S. Appl. No. 10/587,707 (issued as U.S. Pat. No. 7,832,410), May 1, 2017.
R.J. Reynolds Vapor Company, IPR2017-01318, Exhibit 1006—Excerpt of File History for U.S. Appl. No. 12/944,123 (issued as U.S. Pat. No. 8,393,331), May 1, 2017.
R.J. Reynolds Vapor Company, IPR2017-01318, Exhibit 1007—Substitute Specification filed in U.S. Appl. No. 12/944,123 (issued as U.S. Pat. No. 8,393,331), May 1, 2017.
R.J. Reynolds Vapor Company, IPR2017-01318, Exhibit 1008—Declaration of Dr. Robert H. Sturges, May 1, 2017.
R.J. Reynolds Vapor Company, IPR2017-01318, Exhibit 1009—U.S. Pat. No. 8,393,331, May 1, 2017.
R.J. Reynolds Vapor Company, IPR2017-01318, Exhibit 1011—U.S. Pat. No. 8,689,805, May 1, 2017.
R.J. Reynolds Vapor Company, IPR2017-01318, Exhibit 1012—Excerpt of File History for 805 patent, May 1, 2017.
R.J. Reynolds Vapor Company, IPR2017-01318, Exhibit 1013—IPR2016-01859, Paper 8, Decision Denying Institution, May 1, 2017.
R.J. Reynolds Vapor Company, IPR2017-01318, Exhibit 1015—Certified translation of WO2005099494, May 1, 2017.
R.J. Reynolds Vapor Company, IPR2017-01319, Paper 2, Petition for Inter Partes Review of U.S. Pat. No. 9,326,549, May 3, 2017.
R.J. Reynolds Vapor Company, IPR2017-01319, Exhibit 1001—U.S. Pat. No. 9,326,549, May 3, 2017.
R.J. Reynolds Vapor Company, IPR2017-01319, Exhibit 1002—Declaration of Dr. Robert H. Sturges, May 3, 2017.
R.J. Reynolds Vapor Company, IPR2017-01319, Exhibit 1003—CN1233436A, May 3, 2017.
R.J. Reynolds Vapor Company, IPR2017-01319, Exhibit 1004—Certified Translation of CN1233436A to Hongbin, May 3, 2017.
R.J. Reynolds Vapor Company, IPR2017-01319, Exhibit 1005—U.S. Pat. No. 2,057,353, May 3, 2017.
R.J. Reynolds Vapor Company, IPR2017-01319, Exhibit 1006—U.S. Pat. No. 4,947,874, May 3, 2017.
R.J. Reynolds Vapor Company, IPR2017-01319, Exhibit 1007—IPR2014-01300, Paper 8, Institution Decision, May 3, 2017.
R.J. Reynolds Vapor Company, IPR2017-01319, Exhibit 1008—16-cv-1255, *Fontem Ventures B.V. v. R.J. Reynolds Vapor Co.*, Plaintiffs' Preliminary Claim Constructions and Preliminary Identification of Intrinsic and Extrinsic Evidence, May 3, 2017.
R.J. Reynolds Vapor Company, IPR2017-01319, Exhibit 1009—U.S. Pat. No. 6,598,607, May 3, 2017.
R.J. Reynolds Vapor Company, IPR2017-01319, Exhibit 1010—U.S. Pat. No. 4,793,365, May 3, 2017.
R.J. Reynolds Vapor Company, IPR2017-01319, Exhibit 1011—U.S. Pat. No. 5,203,355, May 3, 2017.
R.J. Reynolds Vapor Company, IPR2017-01319, Exhibit 1012—U.S. Pat. No. 2,472,282, May 3, 2017.
R.J. Reynolds Vapor Company, IPR2017-01319, Exhibit 1013—U.S. Pat. No. 2,032,695, May 3, 2017.
R.J. Reynolds Vapor Company, IPR2017-01319, Exhibit 1014—Certified Translation of CN2293957Y, May 3, 2017.
R.J. Reynolds Vapor Company, IPR2017-01319, Exhibit 1015—U.S. Pat. No. 5,743,251, May 3, 2017.
R.J. Reynolds Vapor Company, IPR2017-01319, Exhibit 1016—U.S. Pat. No. 1,514,682, May 3, 2017.
R.J. Reynolds Vapor Company, IPR2017-01319, Exhibit 1017—U.S. Pat. No. 5,745,985, May 3, 2017.

(56) References Cited

OTHER PUBLICATIONS

R.J. Reynolds Vapor Company, IPR2017-01319, Exhibit 1018—U.S. Pat. No. 4,208,005, May 3, 2017.
R.J. Reynolds Vapor Company, IPR2017-01319, Exhibit 1019—U.S. Pat. No. 4,945,448, May 3, 2017.
R.J. Reynolds Vapor Company, IPR2017-01319, Exhibit 1020—Excerpts from James W. Dally, Packaging of Electronic Systems: A Mechanical Engineering Approach (1990), May 3, 2017.
R.J. Reynolds Vapor Company, IPR2017-01319, Exhibit 1021—EP0845220B1, May 3, 2017.
R.J. Reynolds Vapor Company, IPR2017-01319, Exhibit 1022—U.S. Pat. No. 6,155,268, May 3, 2017.
R.J. Reynolds Vapor Company, IPR2017-01319, Exhibit 1023—U.S. Pat. No. 6,501,052, May 3, 2017.
R.J. Reynolds Vapor Company, IPR2017-01319, Exhibit 1024—U.S. Pat. No. 4,981,522, May 3, 2017.
R.J. Reynolds Vapor Company, IPR2017-01319, Exhibit 1025—Excerpts from File History for U.S. Appl. No. 14/719,061 (issued as U.S. Pat. No. 9,326,549), May 3, 2017.
R.J. Reynolds Vapor Company, IPR2017-01319, Exhibit 1026—Eugene A. Avallone, Mark's Standard Handbook for Mechanical Engineers, 15-16 (1978), May 3, 2017.
R.J. Reynolds Vapor Company, IPR2018-00627, Paper 2, Petition for Inter Partes Review of U.S. Pat. No. 9,393,331, Mar. 1, 2018.
R.J. Reynolds Vapor Company, IPR2018-00627, Ex. 1001—U.S. Pat. No. 8,393,331 ("331 patent"), Mar. 1, 2018.
R.J. Reynolds Vapor Company, IPR2018-00627, Ex. 1002—Expert Declaration of Robert Sturges, Ph.D., Mar. 1, 2018.
R.J. Reynolds Vapor Company, IPR2018-00627, Ex. 1003—U.S. Pat. No. 6,155,268 ("Takeuchi"), Mar. 1, 2018.
R.J. Reynolds Vapor Company, IPR2018-00627, Ex. 1004—U.S. Pat. No. 5,743,251 ("Howell"), Mar. 1, 2018.
R.J. Reynolds Vapor Company, IPR2018-00627, Ex. 1005—U.S. Pat. No. 6,598,607 ("Adiga"), Mar. 1, 2018.
R.J. Reynolds Vapor Company, IPR2018-00627, Ex. 1006—U.S. Pat. No. 5,894,841 ("Voges"), Mar. 1, 2018.
R.J. Reynolds Vapor Company, IPR2018-00627, Ex. 1007—U.S. Pat. No. 4,990,939 ("Sekiya"), Mar. 1, 2018.
R.J. Reynolds Vapor Company, IPR2018-00627, Ex. 1008—U.S. Pat. No. 4,771,295 ("Baker"), Mar. 1, 2018.
R.J. Reynolds Vapor Company, IPR2018-00627, Ex. 1009—Institution Decision dated Feb. 19, 2015 (Paper 8), *NJOY, Inc. v. Fontem Holdings 1 B.V.*, IPR2014-01289 (P.T.A.B., petition filed Aug. 14, 2014), Mar. 1, 2018.
R.J. Reynolds Vapor Company, IPR2018-00627, Ex. 1010—Termination Order dated Nov. 24, 2015 (Paper 39), *NJOY, Inc. v. Fontem Holdings 1 B.V.*, IPR2014-01289 (P.T.A.B., petition filed Aug. 14, 2014), Mar. 1, 2018.
R.J. Reynolds Vapor Company, IPR2018-00627, Ex. 1011—Institution Decision dated Dec. 14, 2016 (Paper 11), *Nu Mark LLC v. Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1012—Termination Order dated Jan. 5, 2017 (Paper 16), *Nu Mark LLC v. Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1013—Institution Decision dated Dec. 29, 2016 (Paper 13), *Nu Mark LLC v. Fontem Holdings 1 B.V.*, IPR2016-01438 (P.T.A.B., petition filed Jul. 14, 2016), Mar. 1, 2018.
R.J. Reynolds Vapor Company, IPR2018-00627, Ex. 1014—Compilation Of The 331 Patent File History, Mar. 1, 2018.
R.J. Reynolds Vapor Company, IPR2018-00627, Ex. 1015—U.S. Pat. No. 5,703,633 ("Gehrer"), Mar. 1, 2018.
R.J. Reynolds Vapor Company, IPR2018-00627, Ex. 1016—U.S. Pat. No. 5,745,985 ("Ghosh"), Mar. 1, 2018.
R.J. Reynolds Vapor Company, IPR2018-00627, Ex. 1017—U.S. Pat. No. 4,208,005 ("Nate"), Mar. 1, 2018.
R.J. Reynolds Vapor Company, IPR2018-00627, Ex. 1018—U.S. Pat. No. 4,945,448 ("Bremenour"), Mar. 1, 2018.
R.J. Reynolds Vapor Company, IPR2018-00627, Ex. 1019—Excerpts from James W. Dally, Packaging of Electronic Systems: A Mechanical Engineering Approach (John Corrigan and John M. Morriss eds., 1990) ("Dally"), Mar. 1, 2018.
R.J. Reynolds Vapor Company, IPR2018-00627, Ex. 1020—U.S. Pat. No. 2,057,353 ("Whittemore"), Mar. 1, 2018.
R.J. Reynolds Vapor Company, IPR2018-00627, Ex. 1021—U.S. Pat. No. 3,200,819 ("Gilbert"), Mar. 1, 2018.
R.J. Reynolds Vapor Company, IPR2018-00627, Ex. 1022—U.S. Pat. No. 6,501,052 ("Cox 052"), Mar. 1, 2018.
R.J. Reynolds Vapor Company, IPR2018-00627, Ex. 1023—U.S. Pat. No. 6,234,167 ("Cox 167"), Mar. 1, 2018.
R.J. Reynolds Vapor Company, IPR2018-00627, Ex. 1024—U.S. Pat. No. 5,124,200 ("Mallonee"), Mar. 1, 2018.
R.J. Reynolds Vapor Company, IPR2018-00627, Ex. 1025—U.S. Pat. No. 4,797,692 ("Ims"), Mar. 1, 2018.
R.J. Reynolds Vapor Company, IPR2018-00627, Ex. 1026—U.S. Pat. No. 5,666,977 ("Higgins"), Mar. 1, 2018.
R.J. Reynolds Vapor Company, IPR2018-00627, Ex. 1027—EP Pat. App. Pub. No. EP 0 358 114 A2 ("Brooks 114"), Mar. 1, 2018.
R.J. Reynolds Vapor Company, IPR2018-00627, Ex. 1028—U.S. Pat. No. 7,284,424 ("Kanke"), Mar. 1, 2018.
R.J. Reynolds Vapor Company, IPR2018-00627, Ex. 1029—U.S. Pat. No. 5,224,265 ("Dux"), Mar. 1, 2018.
R.J. Reynolds Vapor Company, IPR2018-00627, Ex. 1030—U.S. Pat. No. 6,620,659 ("Emmma"), Mar. 1, 2018.
R.J. Reynolds Vapor Company, IPR2018-00627, Ex. 1031—U.S. Pat. No. 4,676,237 ("Wood"), Mar. 1, 2018.
R.J. Reynolds Vapor Company, IPR2018-00627, Ex. 1032—Chinese Utility Model Pub. No. 1233436A ("Hongbin") (including certified translation), Mar. 1, 2018.
R.J. Reynolds Vapor Company, IPR2018-00627, Ex. 1033—Excerpts from The Oxford American Dictionary and Thesaurus (Ex. 2007), *Nu Mark LLC v. Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1035—Teleconference Transcript (Ex. 3001), *Nu Mark LLC v. Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1036—Patent Owner's Preliminary Response to Petition for Inter Partes Review dated Oct. 7, 2016 (Paper 8), *Nu Mark LLC v. Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1037—Excerpts from Merriam-Webster's Collegiate Dictionary 11th ed. (Ex. 2003), *Nu Mark LLC v. Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1038—Excerpts from Webster's Unabridged Dictionary 2nd ed. (Ex. 2030), *Nu Mark LLC v. Fontem Holdings 1 B.V.*, IPR2016-01299 (P.T.A.B., petition filed Jun. 28, 2016), Mar. 1, 2018.
R.J. Reynolds Vapor Company, IPR2018-00627, Ex. 1039—Institution Decision dated Feb. 6, 2018 (Paper 8), *Samsung Elecs. Am. v. Uniloc*, IPR2017-01801 (P.T.A.B., petition filed Jul. 20, 2017), Mar. 1, 2018.
R.J. Reynolds Vapor Company, IPR2018-00627, Ex. 1040—Institution Decision dated Feb. 5, 2018 (Paper 9), *Cascades Canada ULC v. SCA Hygiene Prods AB*, IPR2017-01921 (P.T.A.B., petition filed Aug. 7, 2017), Mar. 1, 2018.
R.J. Reynolds Vapor Company, IPR2018-00627, Ex. 1041—Institution Decision dated Jan. 19, 2018 (Paper 9), *Donghee America, Inc. v. Plastic Omnium Advanced Innovation and Research*, IPR2017-01654 (P.T.A.B., petition filed Jun. 21, 2017), Mar. 1, 2018.
R.J. Reynolds Vapor Company, IPR2018-00627, Ex. 1042—Institution Decision dated May 18, 2017 (Paper 9), *Limelight Networks, Inc. v. Mass. Inst. of Tech.*, IPR2017-00249 (P.T.A.B., petition filed Nov. 11, 2016), Mar. 1, 2018.
R.J. Reynolds Vapor Company, IPR2018-00627, Ex. 1043—Institution Decision dated Jul. 15, 2015 (Paper 10), *Microsoft Corp. v. Parallel Networks Licensing, LLC*, IPR2015-00483 (P.T.A.B., petition filed Dec. 23, 2014), Mar. 1, 2018.

(56) References Cited

OTHER PUBLICATIONS

R.J. Reynolds Vapor Company, IPR2018-00627, Ex. 1044—Institution Decision dated Mar. 13, 2013 (Paper 19), *Micron Tech., Inc. v. Bd. of Trs. of the Univ. of Ill.*, IPR2013-00005 (P.T.A.B., petition filed Oct. 2, 2012), Mar. 1, 2018.
R.J. Reynolds Vapor Company, IPR2018-00627, Ex. 1045—Institution Decision dated Jan. 24, 2013 (Paper 18), *Macauto U.S.A. v. BOS GMBH & KG*, IPR2012-00004 (P.T.A.B., petition filed Sep. 16, 2012), Mar. 1, 2018.
R.J. Reynolds Vapor Company, IPR2018-00627, Ex. 1046—Institution Decision dated Dec. 30, 2016 (Paper 11), *R.J. Reynolds Vapor Co. v. Fontem Holdings 1 B.V.*, IPR2016-01272 (P.T.A.B., petition filed Jul. 2, 2016), Mar. 1, 2018.
R.J. Reynolds Vapor Company, IPR2018-00627, Ex. 1047—Final Written Decision dated Jan. 25, 2016 (Paper 39), *Google, Inc. v. Visual Real Estate, Inc.*, IPR2014-01339 (P.T.A.B., petition filed Aug. 20, 2014), Mar. 1, 2018.
R.J. Reynolds Vapor Company, IPR2018-00627, Ex. 1048—Final Written Decision dated Feb. 17, 2016 (Paper 40), *Cisco Sys., Inc., et al. v. Capella Photonics, Inc.*, IPR2014-01276 (P.T.A.B., petition filed Aug. 12, 2014), Mar. 1, 2018.
R.J. Reynolds Vapor Company, IPR2018-00627, Ex. 1049—Final Written Decision dated Mar. 28, 2016 (Paper 20), *RF Controls, LLC v. A-1 Packaging Sols., Inc.*, IPR2014-01536 (P.T.A.B., petition filed Sep. 23, 2014), Mar. 1, 2018.
Sottera, Inc., CV11-0367 Invalidity Contentions, Apr. 12, 2012.
Sottera, Inc., Invalidity Contentions, Exhibit 7, CV11-0367, Apr. 12, 2012.
Sottera, Inc., Invalidity Contentions, Exhibit 8, CV11-0367, Apr. 12, 2012.
U.S. District Court, Central District of California, Markman Hearing/Claim Construction Final Ruling, *Fontem Ventures B.V., et al. v. NJOY, Inc., et al.*, Case No. CV 14-1645-GW (MRWx), Dkt. 133, May 7, 2015, 16 pgs.
U.S. District Court, Central District of California, Rulings on Claims Construction, *Fontem Ventures B.V et al v. NJOY Inc et al*, Case No. 14-cv-01645, Dkt. 65, Jan. 29, 2015, 28 pgs.
U.S. District Court, Middle District of North Carolina, Claim Construction Order, *Fontem Ventures B.V. v. R.J. Reynolds Vapor Company*, Case No. 16-cv-01255, Dkt. 148, Mar. 12, 2018, 8 pgs.
U.S. Appl. No. 10/587,707, Non-Final Office Action, Sep. 1, 2009.
U.S. Appl. No. 14/525,066, Office Action, Sep. 28, 2017.
U.S. Appl. No. 14/525,066, Non-Final Office Action, May 15, 2018.
U.S. Appl. No. 14/525,066, Notice of Allowance, Nov. 2, 2018.
U.S. Appl. No. 12/944,123, Final Office Action, Oct. 30, 2012.
U.S. Appl. No. 12/944,123, Non-Final Office Action, Dec. 13, 2011.
U.S. Appl. No. 13/560,789, Notice of Allowance, May 10, 2013.
U.S. Appl. No. 13/777,927, Final Office Action, Jan. 16, 2014.
U.S. Appl. No. 13/777,927, Office Action, Aug. 16, 2013.
U.S. Appl. No. 14/719,061, Non-Final Office Action, Jul. 8, 2015.
U.S. Appl. No. 14/719,061, Notice of Allowance, Jan. 20, 2016.
U.S. Appl. No. 14/719,923, Non-Final Office Action, Jan. 29, 2016.
U.S. Appl. No. 15/167,825, Notice of Allowance, Jun. 2, 2017.
U.S. Appl. No. 15/167,825, Office Action, Sep. 9, 2016.
U.S. Appl. No. 15/633,434, Office Action, Nov. 7, 2017.
U.S. Appl. No. 15/633,434, Notice of Allowance, Apr. 5, 2018.
U.S. Appl. No. 15/900,430, Non-Final Office Action, May 9, 2018.
U.S. Appl. No. 15/900,430, Notice of Allowance, Jul. 18, 2018.
U.S. Appl. No. 15/900,430, Corrected Notice of Allowability, Aug. 30, 2018.
U.S. Appl. No. 15/990,773, Non-Final Office Action, Oct. 18, 2018.
U.S. Appl. No. 15/990,773, Notice of Allowance, Mar. 7, 2019.
U.S. Appl. No. 16/440,956, Nonfinal Office Action, Sep. 20, 2019.
U.S. Appl. No. 16/440,956, Nonfinal Office Action, Feb. 4, 2020.
U.S. Appl. No. 16/440,956, Notice of Allowance, Apr. 27, 2020.
U.S. Appl. No. 16/839,004, Nonfinal Office Action, Dec. 15, 2020.
U.S. Appl. No. 16/946,289, Nonfinal Office Action, Sep. 30, 2020.
USPTO PTAB, *NJOY Inc. v. Fontem Holdings 1 B.V.*, IPR2014-01289, Paper 8, Decision Instituting Inter Partes Review, Feb. 19, 2015.
USPTO PTAB, *NJOY Inc. v. Fontem Holdings 1 B.V.*, IPR2014-01300, Paper 8, Decision Instituting Inter Partes Review, Feb. 19, 2015.
USPTO PTAB, *NJOY Inc. et al. v. Fontem Holdings 1 B.V.*, IPR2015-01302, Paper 15, Decision Denying Inter Partes Review, Dec. 15, 2015.
USPTO PTAB, *Nu Mark LLC v. Fontem Holdings 1 B.V.*, IPR2016-01283, Paper 12, Decision Denying Inter Partes Review, Nov. 30, 2016.
USPTO PTAB, *Nu Mark LLC v. Fontem Holdings 1 B.V.*, IPR2016-01285, Paper 12, Decision Denying Inter Partes Review, Nov. 30, 2016.
USPTO PTAB, *Nu Mark LLC v. Fontem Holdings 1 B.V.*, IPR2016-01299, Paper 11, Decision Instituting Inter Partes Review, Dec. 14, 2016.
USPTO PTAB, *Nu Mark LLC v. Fontem Holdings 1 B.V.*, IPR2016-01438 Paper 13, Decision Denying Inter Partes Review, Dec. 29, 2016.
USPTO PTAB, *R.J. Reynolds Vapor Co. v. Fontem Holdings 1 B.V.*, IPR2016-01270, Paper 11, Decision Denying Inter Partes Review, Jan. 4, 2017.
USPTO PTAB, *R.J. Reynolds Vapor Co. v. Fontem Holdings 1 B.V.*, IPR2016-01527, Paper 10, Decision Denying Inter Partes Review, Jan. 30, 2017.
USPTO PTAB, *R.J. Reynolds Vapor Co. v. Fontem Holdings 1 B.V.*, IPR2016-01859, Paper 8, Decision Denying Inter Partes Review, Mar. 13, 2017.
USPTO PTAB, *R.J. Reynolds Vapor Co. v. Fontem Holdings 1 B.V.* IPR2018-00627, Paper 10, Decision Instituting Inter Partes Review, Jul. 30, 2018.
U.S. Appl. No. 16/846,255, Notice of Allowance, May 25, 2021.
U.S. Appl. No. 16/839,004, Notice of Allowance, Feb. 26, 2021.

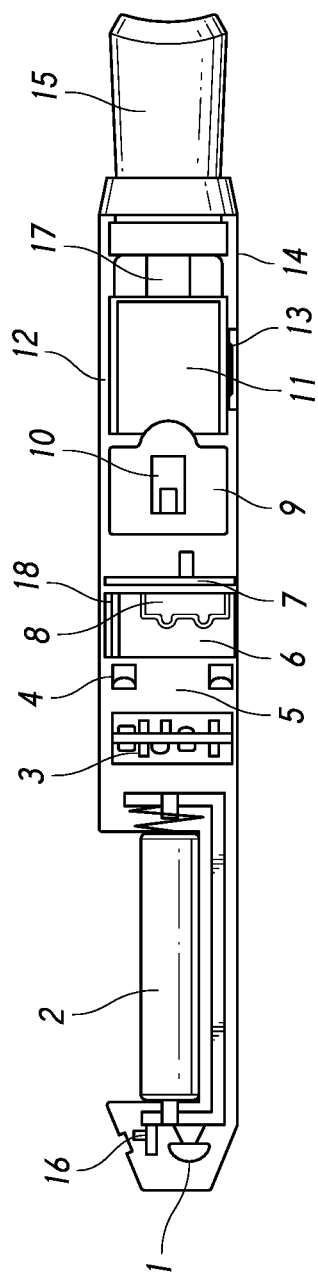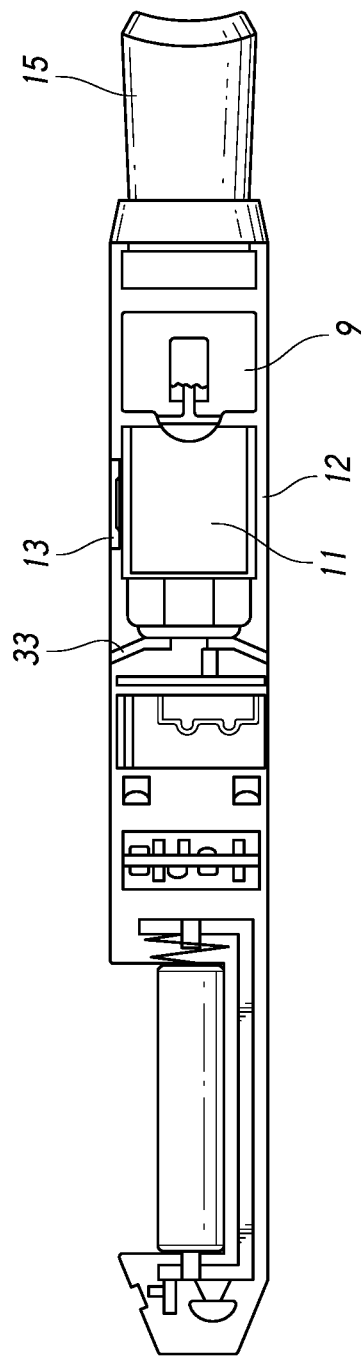

ELECTRONIC CIGARETTE

CROSS REFERENCE TO RELATED APPLICATIONS

This application is a Continuation of U.S. patent application Ser. No. 16/839,004, filed Apr. 2, 2020, which is a Continuation of U.S. patent application Ser. No. 16/440,956 filed Jun. 13, 2019, now U.S. Pat. No. 10,701,982, which is a Continuation of U.S. patent application Ser. No. 15/990,773, filed May 28, 2018, now U.S. Pat. No. 10,349,682, which is a Continuation of U.S. patent application Ser. No. 14/525,066, filed Oct. 27, 2014, now U.S. Pat. No. 10,238,144, which is a Continuation of U.S. patent application Ser. No. 13/777,927, filed Feb. 26, 2013, now U.S. Pat. No. 8,893,726, which is a Divisional of U.S. patent application Ser. No. 13/560,789, filed Jul. 27, 2012, now U.S. Pat. No. 8,490,628, which is a Continuation of U.S. patent application Ser. No. 12/944,123, filed Nov. 11, 2010, now U.S. Pat. No. 8,393,331, which is a Continuation of U.S. patent application Ser. No. 10/587,707, filed Mar. 9, 2007, now U.S. Pat. No. 7,832,410 which is the U.S. National Phase Application of International PCT Application No. PCT/CN05/00337, filed Mar. 18, 2005, which claims the benefit of Chinese Patent Application No. 200420031182.0, filed Apr. 14, 2004. The Applications listed above are incorporated herein by reference.

TECHNICAL FIELD

The present invention relates to an electronic cigarette, in particular to an electronic atomization cigarette that contains only nicotine without tar.

BACKGROUND ART

Although it is commonly known that "smoking is harmful to your health", the number of smokers worldwide is up to 1 billion, and the number is increasing every year. According to the statistical data from the World Health Organization, about 4.9 million people die of smoking diseases each year. Although smoking may cause serious respiratory diseases and cancer, it remains extremely difficult for smokers to quit smoking completely.

The active ingredient in a cigarette is nicotine. During smoking, nicotine, along with tar aerosol droplets, enter the smoker's alveolus and are rapidly absorbed. The nicotine then affects the receptors of the smoker's central nervous system.

Nicotine is a kind of alkaloid with low molecular weight. A small dose of nicotine is essentially harmless to human body and its half-life in blood is quite short. The major harmful substance in tobacco is tar. Tar in tobacco is composed of thousands of ingredients. Several of these are cancerogenic.

Some cigarette substitutes that contain only nicotine without tar have been proposed. Many of them, such as "nicotine patch", "nicotine mouthwash", "nicotine chewing gum", "nicotine drink" etc., are made of pure nicotine. Although these cigarette substitutes are free from tar, their major disadvantage is that an effective peak concentration cannot be reached in the blood of a smoker due to slow absorption of nicotine. In addition, these cigarette substitutes cannot satisfy habitual smoking actions of a smoker, for example, inhaling action, and thus are not likely to be widely accepted as effective substitutes for smoking.

THE SUMMARY OF THE INVENTION

An electronic atomization cigarette that functions as substitutes for quitting smoking and cigarette substitutes includes a shell; a mouthpiece; an air inlet provided in the external wall of the shell; an electronic circuit board, a sensor, an atomizer, and a liquid-supply within the shell. A stream passage is provided on one side of the sensor. An atomization cavity is arranged in the atomizer. The liquid-supply is in contact with the atomizer.

BRIEF DESCRIPTION OF THE DRAWINGS

FIG. 1 is a schematic diagram of an overall structure;
FIG. 2 is a schematic diagram of another overall structure.

DETAILED DESCRIPTION

Embodiment 1

Figure 3:
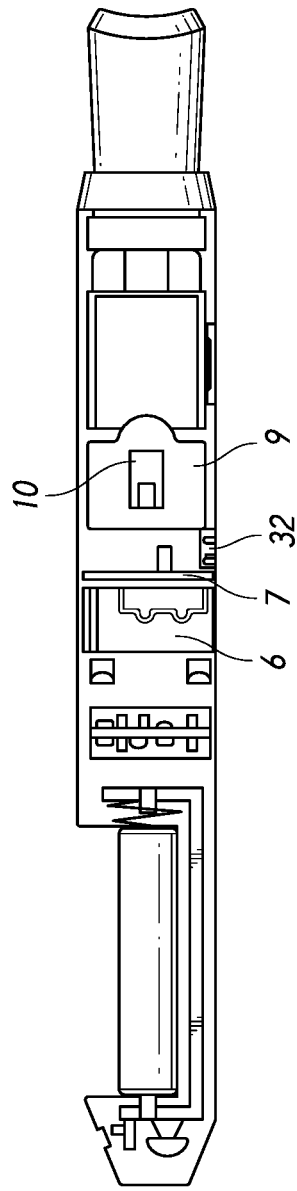
FIG. 3 is a schematic diagram of an overall structure with a display screen.

As shown in FIG. 1, an air inlet 4 is provided on the external wall of the shell 14. A LED 1, a cell 2, an electronic circuit board 3, a normal pressure cavity 5, a sensor 6, a vapor-liquid separator 7, an atomizer 9, a liquid-supplying bottle 11 and a mouthpiece 15 are sequentially provided within the shell 14. The electronic circuit board 3 comprises an electronic switching circuit and a high frequency generator.

Figure 4:
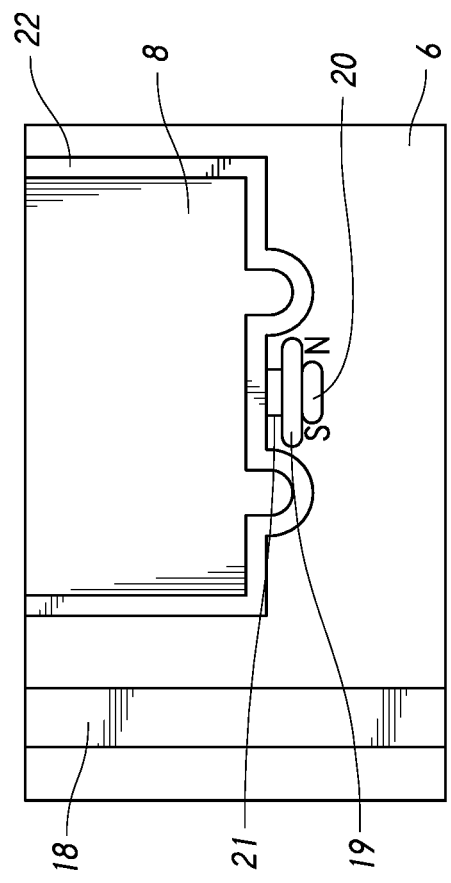
FIG. 4 is a structural diagram of a sensor.

As shown in FIG. 4, a negative pressure cavity 8 is provided in the sensor 6 and is separated from the sensor 6 by a film 22. A first magnetic steel 20, a second magnetic steel 21 and a Reed switch 19 arranged between them is also provided within the sensor 6. The second magnetic steel 21 is attached to the film 22. The atomizer 9 is in contact with the liquid-supplying bottle 11 via the bulge 36, and the atomization cavity 10 is provided in the atomizer 9.

Figure 6:
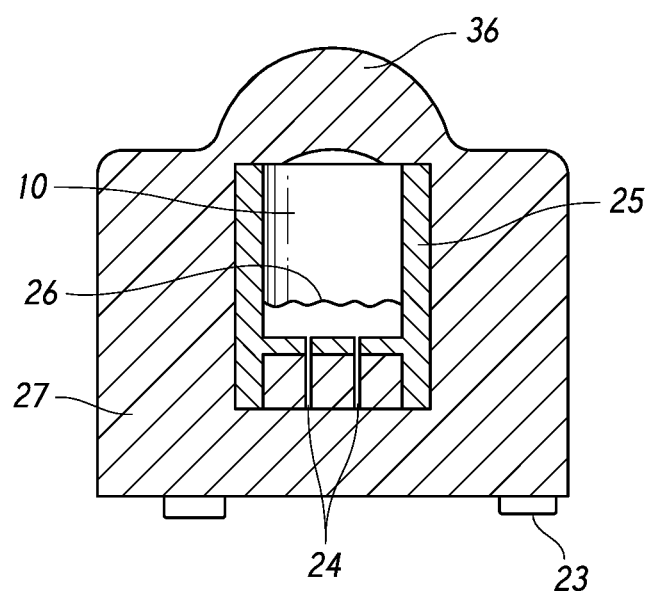
FIG. 6 is a structural diagram of an atomizer.
Figure 7:
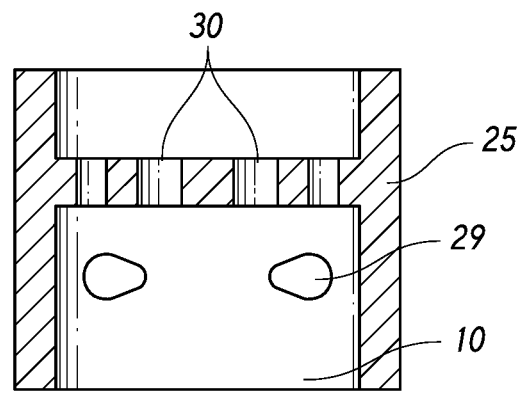
FIG. 7 is a structural diagram of the ceramic member in an atomizer.

As shown in FIGS. 6 and 7, the overflow hole 29 is provided on the wall 25 of the atomization cavity 10. A heating element 26, which can be made of platinum wire, nickel chromium alloy or iron chromium aluminum alloy wire with rare earth element, is provided within the cavity, and can also be made into a sheet form with conductive ceramics or PTC ceramics. An ejection hole is provided on the side opposite to the heating element 26. The ejection hole can be determined to select either the long stream ejection hole 24 or the short stream ejection hole 30, depending on the material used for the atomization cavity wall 25. The long stream ejection hole 24 can employ slot structure of 0.1 mm-1.3 mm or circular hole structure with a single and multiple holes. The short stream ejection hole 30 has the diameter of about 0.3 mm-1.3 mm.

Figure 9:
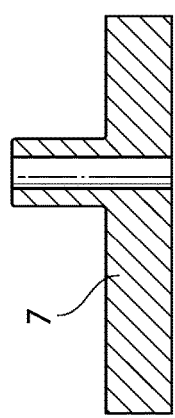
FIG. 9 is a structural diagram of a vapor-liquid separator.

The atomization cavity wall 25 is surrounded with the porous body 27, which can be made of foam nickel, stainless steel fiber felt, high molecule polymer foam and foam ceramic. A first piezoelectric element 23 is also provided on the atomizer 9. The atomization cavity wall 25 can be made of aluminum oxide or ceramic. As shown in FIG. 9, a through hole is provided on the vapor-liquid separator 7, and can be made of plastic or silicon rubber. As shown in FIG. 2, a retaining ring 13 for locking the liquid-supplying bottle 11 is provided between one side of the liquid-supplying bottle 11 and the shell 14. An aerosol passage 12 is provided on the other side of the liquid-supplying bottle.

Figure 11:
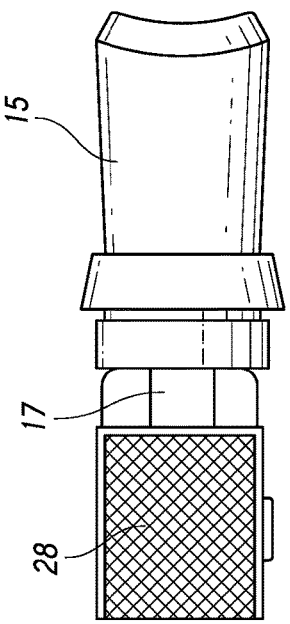
FIG. 11 is a structural diagram of the connection of a liquid-supplying bottle and a mouthpiece.

As shown in FIG. 11, the solution storage porous body 28 is provided in the liquid-supplying bottle, and can be filled with polypropylene fiber, terylene fiber or nylon fiber, or be filled with plastic shaped by foaming, such as polyamine resin foam column or polypropylene foam column. Alternatively, it may be made of a column formed by molding polyvinyl chloride, polypropylene, polycarbonate into a stack of laminated layers. The air inlet 4, normal pressure cavity 5, vapor-liquid separator 7, atomizer 9, aerosol passage 12, gas vent 17, mouthpiece 15 are sequentially interconnected.

Figure 12:
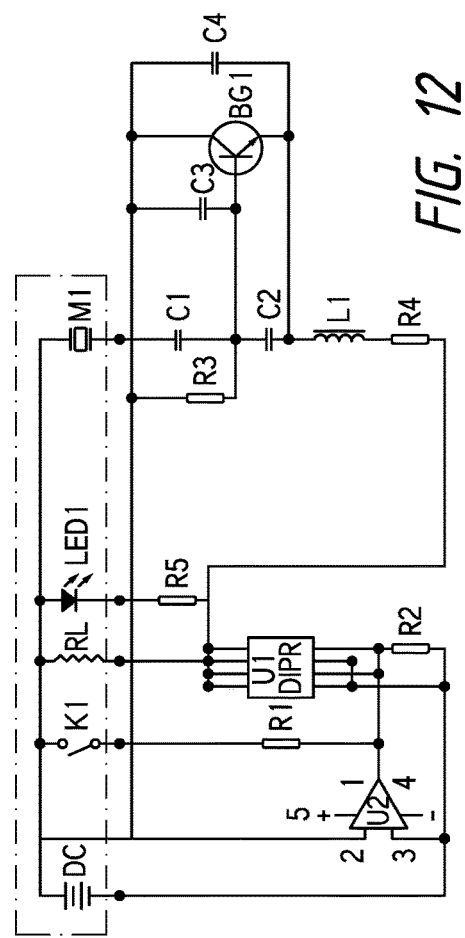
FIG. 12 is a functional diagram of a circuit.

As shown in the functional diagram of the circuit in FIG. 12, K1 refers to the Reed switch 19, RL refers to the heating element 26, LED1 refers to the Light Emitting Diode 1, U2 refers to the low voltage detecting element used for the over-discharging protection of the lithium cell, M1 refers to the first piezoelectric element 23, and C1, C2, R3, L1, C3, BG, M1 collectively constitute a Colpitts oscillator. The operating principle of the circuit is as follows: when K1 is closed, U1, i.e., the field effect power transistor, is turned on, RL starts, and the Colpitts oscillator starts oscillating, M1 will provide the high frequency mechanical oscillatory wave to the atomizer 9.

When a smoker smokes, the mouthpiece 15 is under negative pressure. The air pressure difference or high speed stream between the normal pressure cavity 5 and the negative pressure cavity 8 causes the sensor 6 to output an actuating signal, the electronic circuit board 3 connected therewith goes into operation. Now the ripple film 22 in the sensor 6 is deformed to take the second magnetic steel 21 away from the Reed switch 19. The Reed switch 19 is then closed (i.e., K1 is closed) under the effect of the excessive magnetic line of force from the first magnetic steel 20, starting the field effect power transistor electronic switch (i.e., U1 is opened). The high frequency oscillator may uses the Colpitts oscillator with the frequency of 550 KHz-8 MHz. The automatic fine-adjusting element in the circuit resonates with the first piezoelectric element 23. The LED 1 can be lit under the supply of the rechargeable battery 2.

Air enters the normal pressure cavity 5 through the air inlet 4, passes through the air passage 18 of the sensor and then the through hole in the vapor-liquid separator 7, and flows into the atomization cavity 10 in the atomizer 9. The high speed stream passing through the ejection hole drives the nicotine solution in the porous body 27 to eject into the atomization cavity 10 in the form of droplets, where the nicotine solution is subjected to the ultrasonic atomization by the first piezoelectric element 23 and is further atomized by the heating element 26.

After the atomization the droplets with large diameters stick to the wall under the action of eddy flow and are reabsorbed by the porous body 27 via the overflow hole 29. Droplets with small diameters float in stream and form aerosols, which are sucked out via the aerosol passage 12, gas vent 17 and mouthpiece 15. The solution storage porous body 28 in the liquid-supplying bottle 11 is in contact with the bulge 36 on the atomizer 9, thereby achieving the capillary infiltration liquid-supplying.

The mouthpiece 15 is threaded. When the nicotine solution in the liquid-supplying bottle 11 is used up, users can screw the mouthpiece 15 out to take the liquid-supplying bottle 11 out, refill the liquid-supplying bottle 11 with the nicotine solution, put the liquid-supplying bottle 11 into the shell 14 again, and then screw the mouthpiece 15.

The Reed switch 19, the first magnetic steel 20, the second magnetic steel 21, the ripple film 22 can be replaced by a semiconductor strain gauge with sealed film, which is mounted in the place of the sensor ripple film.

Figure 8:
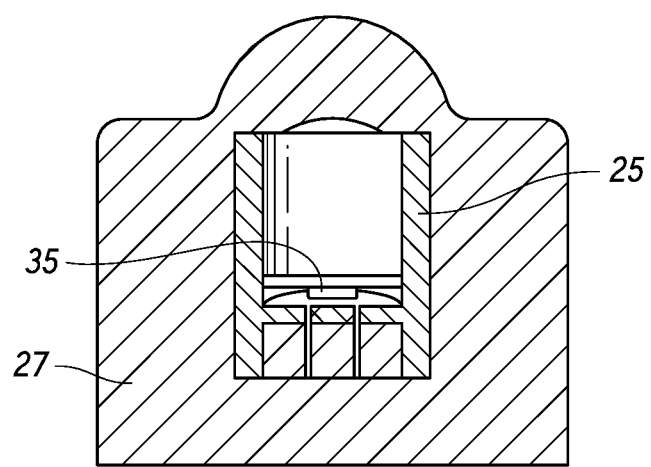
FIG. 8 is a structural diagram of another atomizer.

To simplify the design, the first piezoelectric element 23 on the atomizer 9 can be omitted, and the atomization of the nicotine solution will be made only by the heating element 26. The size of such an atomizer can be made smaller, and the structure of the connection of the whole electronic atomization cigarette is the same as the embodiment 1. In addition, as shown FIG. 8, the first piezoelectric element 23 and the heating element 26 in the atomizer 9 can be omitted, an additional second piezoelectric element 35 in the form of platen with a single layer or multiple laminated layers can be arranged in the atomization cavity, and the stream passing through the ejection hole vibrates the focus at the center of the second piezoelectric element 35 to achieve the effect of strong ultrasonic atomization.

Figure 10:
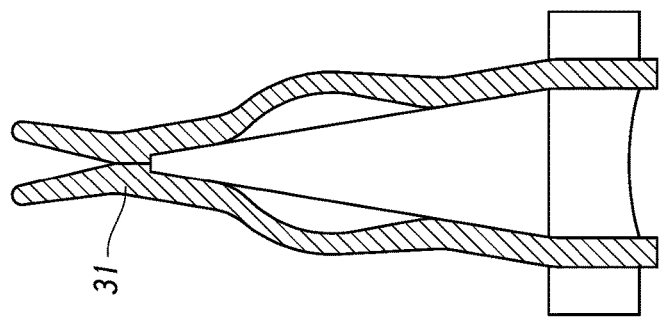
FIG. 10 is a structural diagram of another vapor-liquid separator.

As shown in FIG. 10, a silicon gel check valve 31 may cover the outside of the through hole on the vapor-liquid separator 7. During smoking, a stream reaches the through hole, as the air pressure in the through hole increases, the silicon gel check valve 31 is opened and the stream passes; otherwise, the silicon gel check valve 31 is closed.

Figure 5:
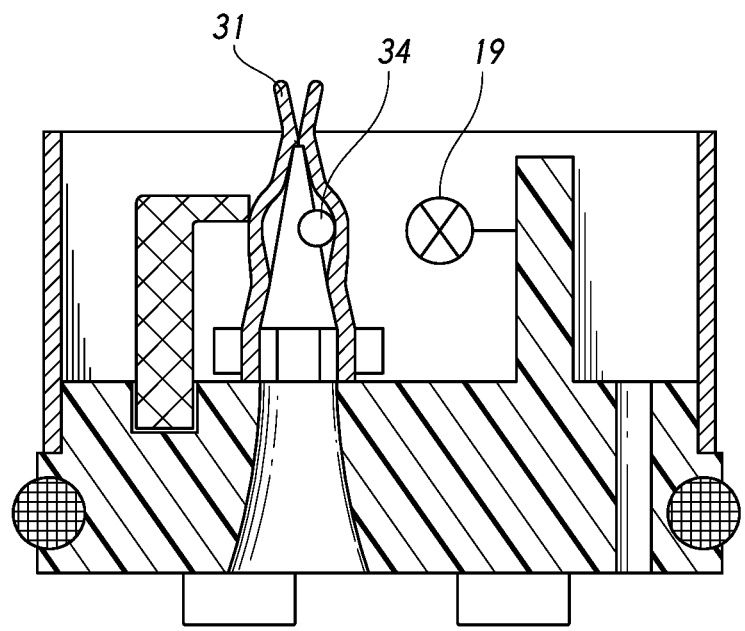
FIG. 5 is a structural diagram of a sensor with a silicon gel check valve.

As shown in FIG. 5, the sensor 6 may also be designed into a structure with the silicon gel check valve 31. During smoking, the stream comes into the silicon gel check valve 31, the air pressure increases and the air expands, the third magnetic steel 34 in the valve approaches the Reed switch 19 gradually until the Reed switch is closed and the circuit is turned on, and the air outlet of the silicon gel check valve 31 is opened with the increment of the air pressure difference. The Reed switch 19 can also be made of Hall device or magneto diode or magneto triode instead.

Embodiment 2

As shown in FIG. 2, to improve the liquid-supplying state, the liquid-supplying bottle 11 is arranged between the vapor-liquid separator 7 and the atomizer 9. A spring piece 33 for pressing the liquid-supplying bottle 11 on the atomizer 9 is provided on one end of the liquid-supplying bottle 11. Other components and their functions are the same as those in the embodiment 1.

On the inner wall of the shell 14 of the electronic atomization cigarette described in the embodiment 1 and 2, a digital display screen 32 for showing the smoking times per day and the cell capacity can be also provided. The sensor 6 uses a linear signal output, which is proportional to the suction force (i.e., the stronger one sucks, the longer the time of operation is), the atomizer 9 operates in the linear mode, thereby simulating a cigarette that looks like a normal cigarette.

Within the shell 14, the microswitch 16 is connected to the sensor 6 in parallel and used for manually cleaning. When users do not smoke, they press the microswitch 16 to start the sensor 6 connected therewith in parallel, or clean the residue or other impurity substances within the shell 14.

The nicotine solution for atomization contains 0.4-3.5% nicotine, 0.05-2% cigarette essence, 0.1-3.1% organic acid, 0.1-0.5% anti-oxidation agent, and the rest is 1,2-propylene glycol.

I claim:

1. An electronic cigarette, comprising:
a housing having an inlet;
a mouthpiece at one end of the housing;
the mouthpiece on a cartridge holding a liquid supply, the cartridge removable from the housing;
an air flow channel in the housing connecting the inlet to an outlet in the mouthpiece; and
an atomizer assembly in the housing between the inlet and the outlet, the atomizer assembly including a ceramic porous component having a atomization cavity, liquid from the liquid supply contacting the ceramic porous component, the atomizer assembly having a heating element oriented perpendicular to a longitudinal axis of the housing.

2. The electronic cigarette of claim 1 wherein the cavity has a first end facing the liquid supply.

3. The electronic cigarette of claim 1 wherein the heating element comprises a sheet form of conductive material.

4. The electronic cigarette of claim 1 further including a sensor in the housing, the sensor electrically connected to an electronic circuit board.

5. The electronic cigarette of claim 4 further including a plastic or silicon separator positioned next to the sensor, the separator having a through hole.

6. The electronic cigarette of claim 4 further comprising an LED electrically connected to the electronic circuit board; and
a retaining element on a side of the liquid supply, a first end of the cartridge configured to be inserted into the housing.

7. The electronic cigarette of claim 1 wherein the liquid supply is cylindrical and parallel to the longitudinal axis of the housing.

8. The electronic cigarette of claim 1 wherein the ceramic porous component is foam ceramic.

9. An electronic cigarette, comprising:
a housing;
an inlet in the housing;
a mouthpiece on a cartridge inserted into the housing, the cartridge holding a liquid in a liquid supply;
an air flow channel in the housing connecting the inlet to an outlet in the mouthpiece;
an atomizer in the housing between the inlet and the outlet, the atomizer including a ceramic porous component having a cavity facing the liquid supply;
the atomizer having a heating element oriented perpendicular to a longitudinal axis of the housing, the heating element comprising a sheet form of conductive material;
with liquid from the liquid supply contacting the cavity of the ceramic porous component and the ceramic porous component configured to absorb the liquid and to move the liquid towards the heating element via capillary action; and
a sensor and an LED electrically connected to an electronic circuit board in the housing.

10. The electronic cigarette of claim 9 further including a plastic or silicon separator positioned next to the sensor, the separator having a through hole.

* * * * *